United States Patent
Sato et al.

(10) Patent No.: US 7,956,036 B2
(45) Date of Patent: Jun. 7, 2011

(54) POLYPEPTIDE AND DNA THEREOF USEFUL AS A NEOVASCULAR MARKER

(75) Inventors: Yasufumi Sato, Sendai (JP); Hikaru Sonoda, Toyonaka (JP); Hideki Ohta, Toyonaka (JP)

(73) Assignees: Yasufumi Sato, Sendai-Shi, Miyagi (JP); Shionogi & Co., Ltd., Osaka-Shi, Osaka (JP)

( * ) Notice: Subject to any disclaimer, the term of this patent is extended or adjusted under 35 U.S.C. 154(b) by 585 days.

(21) Appl. No.: 12/027,873

(22) Filed: Feb. 7, 2008

(65) Prior Publication Data

US 2008/0269129 A1 Oct. 30, 2008

Related U.S. Application Data

(62) Division of application No. 10/476,985, filed as application No. PCT/JP02/04251 on Apr. 26, 2002, now abandoned.

(30) Foreign Application Priority Data

May 7, 2001 (JP) .................................. 2001-136179

(51) Int. Cl.
| | |
|---|---|
| *C12N 5/00* | (2006.01) |
| *A61K 38/17* | (2006.01) |
| *A61K 31/711* | (2006.01) |
| *C12Q 1/68* | (2006.01) |
| *A61P 35/00* | (2006.01) |

(52) U.S. Cl. ................. 514/12; 435/6; 435/375; 514/44
(58) Field of Classification Search .................. None
See application file for complete search history.

(56) References Cited

U.S. PATENT DOCUMENTS 5,474,796 A 12/1995 Brennan

FOREIGN PATENT DOCUMENTS

WO WO-01/57182 A2 8/2001

OTHER PUBLICATIONS

GenBank—KIAA 1036 sequence (1999).*
Kikuno et al. (DNA research. 1999; 6: 197-205).*
Shimizu et al. (Biochem Biophys Res Commun. 2005; 327(3): 700-706).*
O'Reilly et al. (Cell. 1997; 88:277-285).*
Li et al. (Journal of Biological Chemistry. 2000; 275(38): 29823-29828).*
Dulak et al. (Eur. Surg 2002; 34(2): 101-104).*
Lathi et al. (Anesth Analog 2001; 92; 19-25).*
Anderson, B. et al., Analytical Biochemistry 236, pp. 107-113, Article No. 0138, (1996).
Angiogenesis, NCBI, GDS495/40266_at dataset, 2003.
Asano, M. et al., Cancer Research, vol. 55, pp. 5296-5301, Nov. 15, 1995.
Carmeliet, P., et al. Nature, vol. 407, pp. 249-257, Sep. 14, 2000.
Cerebellar cortex in schizophrenia, NCBI, GDS1917/1556423_at, 2006.
Database EMBL, Ohara et al., Homo sapiens mRNA for K1AA1036 protein, Database Accession No. AB028959.
GenBank Accession No. AB028959.
Inoue, Mayumi et al., Vascular Endothelial Growth Factor (VEGF) Expression in Human Coronary Atherosclerotic Lesions, Circulation, vol. 98, pp. 2108-2116, 1998.
Kasama, T., et al., Expression of Vascular Endothelial Growth Factor by Synovial Fluid Neutrophils in Rheumatoid Arthritis (RA), Clin Exp Immunol, vol. 121, pp. 533-538, 2000.
Kikuno, R., et al., Prediction of the coding sequences of unidentified human genes. XIV. The complete sequences of 100 new cDNA clones from brain which code for large proteins in vitro, DNA Res., vol. 6, No. 3, pp. 197-205, 1999.
Lip, Peck-Lin, et al., Age-related Macular Degeneration is Associated with Increased Vascular Endothelial Growth Factor, Hemorheology and Endothelial Dysfunction, Opthalmology vol. 108, No. 4, pp. 705-710, Apr. 2001.
Mustonen, Tuija et al., Endothelial Receptor Tyrosine Kinases Involved in Angiogenesis, The Journal of Cell Biology, vol. 129, pp. 895-898, 1995.
Non-melanoma skin cancer, NCBI, GDS2200/203940_at.
Prostate cancer progression, 2005, NCBI, GDS1439/230546_at.
Shinoda, Kei et al., Comparison of the Levels of Hepatocyte Growth Factor and Vascular Endothelial Growth Factor in Aqueous Fluid and Serum With Grades of Retinopathy in Patients With Diabetes melitus. J. Ophthalmol., vol. 83, pp. 834-837, 1999.

* cited by examiner

*Primary Examiner* — Scott Long
(74) *Attorney, Agent, or Firm* — Birch, Stewart, Kolasch & Birch, LLP

(57) ABSTRACT

A marker for neovascularization, vascular disease, inflammatory disease, entoptic neovascular disease, reproductive system disease, central nervous system disease and cancer, the method of detection of the marker and a diagnosis kit of the diseases are provided. Additionally, therapeutic agents of the diseases are provided.
The expression of KIAA1036 is enhanced in ovarian cancer and large bowel cancer and KIAA1036 expresses in umbilical vein endothelial cell and inhibits DNA synthesis in the cells, cell migrating and lumen formation. Therefore KIAA1036 is useful as a marker for neovascularization, vascular disease, inflammatory disease, entoptic neovascular disease, reproductive system disease, central nervous system disease or cancer. Additionally, KIAA1036 is useful for screening of agonists, antagonists, DNA synthesis inhibitors, cell migrating inhibitors and neovascular inhibitors. The substances obtained by the screening, KIAA1036 and the antibodies are useful as therapeutic agents the above disease.

8 Claims, 5 Drawing Sheets

Figure. 1

```
Query:  614  MWKHVAKIHPDGEKVAQRIRGATDLPKIPIPSVPTFQPSTPVPERLEAVQRYIRELQYNH  793
             MW HVAK+HP G ++   IR A  L K  IP VP ++ S  +P+ L+A+Q Y++ LQYNH
Sbjct:    1  MWMHVAKVHPKGGEMVGAIRNAAFLAKPSIPQVPNYRLSMTIPDWLQAIQNYMKTLQYNH   60

Query:  794  TGTQFFEIKKSRPLTGLMDLAKEMTKEALPIKCLEAVILGIYLTNSMPTLERFPISFKTY  973
             TGTQFFEI+K RPL+GLM+ AKEMT+E+LPIKCLEAVILGIYLTN  P++ERFPISFKTY
Sbjct:   61  TGTQFFEIRKMRPLSGLMETAKEMTRESLPIKCLEAVILGIYLTNGQPSIERFPISFKTY  120

Query:  974  FSGNYFRHIVLGVNFAGRYGALGMSRREDLMYKPPAFRTLSELVLDFEAAYGRCWHVLKK  1153
             FSGNYF H+VLG+   GRYG+LGMSRR +LM KP  FRTLS+L+ DFE +Y + H +KK
Sbjct:  121  FSGNYFHHVVLGIYCNGRYGSLGMSRRAELMDKPLTFRTLSDLIFDFEDSYKKYLHTVKK  180

Query: 1154  VKLGQSVSHDPHSVEQIEWKHSVLDVERLGRDDFRKELERHARDMRLKIGKGTGPPSPTK  1333
             VK+G  V H+PHS + IEWK  VL+V ++ R D RKELE++ARDMR+KI K    SPT+
Sbjct:  181  VKIGLYVPHEPHSFQPIEWKQLVLNVSKMLRADIRKELEKYARDMRMKILKPASAHSPTQ  240

Query: 1334  DRKKDVS-SPQRAQSSPHRRNSRSERRPS-GDKKTSEPKAMPDLNGYQIRV  1480
             R +  S  SP+R Q+SP RR  R E+ P+  +KK ++    + ++ GYQIR+
Sbjct:  241  VRSRGKSLSPRRRQASPPRRLGRREKSPALPEKKVADLSTLNEV-GYQIRI  290
```

Figure. 3

| patient | age | sex | cancer | Expression ration of KIAA1036 (Cancer/Normal) |
|---|---|---|---|---|
| 1 | 61 | Female | ovarian cancer | 2.73 |
| 2 | 41 | Female | ovarian cancer | 2.73 |
| 3 | 40 | Female | ovarian cancer | 1.44 |
| 4 | 60 | Female | ovarian cancer | 3.47 |
| 5 | 81 | Male | colon cancer | 1.72 |
| 6 | 68 | Male | colon cancer | 1.25 |
| 7 | 64 | Male | colon cancer | 1.21 |
| 8 | 60 | Male | colon cancer | 3.05 |
| 9 | 61 | Female | colon cancer | 3.88 |
| 10 | 75 | Female | colon cancer | 2.1 |
| 11 | 69 | Female | colon cancer | 2.53 |
| 12 | 35 | Female | colon cancer | 1.7 |
| 13 | 58 | Male | colon cancer | 1.56 |
| 14 | 79 | Female | colon cancer | 1.38 |
| 15 | 51 | Female | colon cancer | 1.79 |

1: no addition
2: KIAA1036 1nM
3: KIAA1036 10nM
4: VEGF 1nM
5: VEGF 1nM
 +KIAA1036 1nM
6: VEGF 1nM
 +KIAA1036 10nM 1: no addition
2: KIAA1036 1nM
3: KIAA1036 10nM
4: VEGF 0.25nM
5: VEGF 0.25nM
   +KIAA1036 1nM
6: VEGF 0.25nM
   +KIAA1036 10nM

SEQUENCE LISTING

```
<160> NUMBER OF SEQ ID NOS: 7

<210> SEQ ID NO 1
<211> LENGTH: 5481
<212> TYPE: DNA
<213> ORGANISM: Homo sapiens
<220> FEATURE:
<221> NAME/KEY: CDS
<222> LOCATION: (386)..(1480)
```

```
<300> PUBLICATION INFORMATION:
<308> DATABASE ACCESSION NUMBER: Genebank/XM#007415
<309> DATABASE ENTRY DATE: 2000-11-17

<400> SEQUENCE: 1
ccgctggtcc gagctgtctg gcctcagttt ccctccgact tttctccgct ctgccagccc        60
tcactgctgc ccgtcattgt tctcgcagtt agatgggggt gctttgtgac ggctgccaag       120
ttggggtgtg ttctctttat ccgttttttc aaacagaaca aggcctccaa ggctgacccc       180 agacaacccca ccccctcgga ccctaattca ccttattgca ctgatttttt ttatcaagtc      240 gtatttatt gtacaggagc cacgccctga tttcttaaag gcgccttgca ctctggccat        300
gtgttatctc tgcagccggt gtgtgggagg cctcttgtga gccagttgtt ttcccgcctc       360
caccaccccc ctcgaagatt taggg atg cca ggg ggg aag aag gtg gct ggg          412
                              Met Pro Gly Gly Lys Lys Val Ala Gly
                                1               5 ggt ggc agc agc ggt gcc act cca acg tcc gct gcg gcc acc gcc ccc          460
Gly Gly Ser Ser Gly Ala Thr Pro Thr Ser Ala Ala Ala Thr Ala Pro
 10              15                  20                  25 tct ggg gtc agg cgt ttg gag acc agc gaa gga acc tca gcc cag aga          508
Ser Gly Val Arg Arg Leu Glu Thr Ser Glu Gly Thr Ser Ala Gln Arg
         30                  35                  40 gat gag gag cca gaa gag gaa ggg gaa gag gac ctg cga gac gga ggc          556
Asp Glu Glu Pro Glu Glu Glu Gly Glu Glu Asp Leu Arg Asp Gly Gly
                 45                  50                  55 gtc ccc ttc ttt gtc aac cgg ggt ggg cta cct gtg gat gag gcc acc          604
Val Pro Phe Phe Val Asn Arg Gly Gly Leu Pro Val Asp Glu Ala Thr
             60                  65                  70 tgg gaa agg atg tgg aaa cac gtg gcc aag atc cac ccc gat gga gag          652
Trp Glu Arg Met Trp Lys His Val Ala Lys Ile His Pro Asp Gly Glu
 75                  80                  85 aag gtg gcg caa cgg atc cgt ggg gcc aca gac ctg ccc aag atc ccc          700
Lys Val Ala Gln Arg Ile Arg Gly Ala Thr Asp Leu Pro Lys Ile Pro
 90                  95                 100                 105 ata ccg agt gtg cct acg ttc cag ccg tct aca cct gtc cct gag cgc          748
Ile Pro Ser Val Pro Thr Phe Gln Pro Ser Thr Pro Val Pro Glu Arg
                110                 115                 120 ctg gaa gct gtg cag cgc tat atc aga gag ctg cag tac aat cac aca          796
Leu Glu Ala Val Gln Arg Tyr Ile Arg Glu Leu Gln Tyr Asn His Thr
            125                 130                 135 ggg aca cag ttc ttt gaa att aag aag agc aga cct ctg aca ggg ctg          844
Gly Thr Gln Phe Phe Glu Ile Lys Lys Ser Arg Pro Leu Thr Gly Leu
        140                 145                 150 atg gac ctg gcc aag gaa atg acc aaa gag gcc ctg cca atc aaa tgc          892
Met Asp Leu Ala Lys Glu Met Thr Lys Glu Ala Leu Pro Ile Lys Cys
155                 160                 165 ctg gaa gcc gtg atc ctg gga att tac ctc acc aac agc atg ccc acc          940
Leu Glu Ala Val Ile Leu Gly Ile Tyr Leu Thr Asn Ser Met Pro Thr
170                 175                 180                 185 ctg gag cgc ttc ccc atc agc ttc aag acc tac ttc tca ggg aac tac          988
Leu Glu Arg Phe Pro Ile Ser Phe Lys Thr Tyr Phe Ser Gly Asn Tyr
                190                 195                 200 ttc cgc cac atc gtg ctg ggg gtg aac ttc gcg ggc cgc tac ggt gcg         1036
Phe Arg His Ile Val Leu Gly Val Asn Phe Ala Gly Arg Tyr Gly Ala
            205                 210                 215 ctg ggc atg agt cgg cgc gag gac ctg atg tac aag ccg ccc gcc ttc         1084
Leu Gly Met Ser Arg Arg Glu Asp Leu Met Tyr Lys Pro Pro Ala Phe
        220                 225                 230 cgc acg ctc agc gag ctc gtg ctg gac ttc gag gcc gcc tac ggc cgc         1132
Arg Thr Leu Ser Glu Leu Val Leu Asp Phe Glu Ala Ala Tyr Gly Arg
```

-continued

```
                 235                 240                 245
tgc tgg cac gtg ctc aag aag gtg aag ctg ggc cag agc gtg tca cac      1180
Cys Trp His Val Leu Lys Lys Val Lys Leu Gly Gln Ser Val Ser His
250                 255                 260                 265 gac ccg cac agc gtg gag cag atc gag tgg aag cac tcg gtg ctg gac      1228
Asp Pro His Ser Val Glu Gln Ile Glu Trp Lys His Ser Val Leu Asp
                270                 275                 280 gtg gag cgc ctg ggc cgc gat gac ttc cgc aag gag ctg gag cgc cac      1276
Val Glu Arg Leu Gly Arg Asp Asp Phe Arg Lys Glu Leu Glu Arg His
            285                 290                 295 gcc cgc gac atg cgg ctc aag att ggc aaa ggg acg ggc cct ccc tct      1324
Ala Arg Asp Met Arg Leu Lys Ile Gly Lys Gly Thr Gly Pro Pro Ser
        300                 305                 310 ccc acc aag gac cgg aag aag gat gtt tct tcc ccg cag cgg gcc cag      1372
Pro Thr Lys Asp Arg Lys Lys Asp Val Ser Ser Pro Gln Arg Ala Gln
    315                 320                 325 tcc agc ccc cac cgc agg aac agc cgc agt gaa aga cgg ccc tcg ggt      1420
Ser Ser Pro His Arg Arg Asn Ser Arg Ser Glu Arg Arg Pro Ser Gly
330                 335                 340                 345 gac aag aag act tcc gag ccc aaa gcc atg cca gac ctt aac ggg tac      1468
Asp Lys Lys Thr Ser Glu Pro Lys Ala Met Pro Asp Leu Asn Gly Tyr
                350                 355                 360 cag atc cgg gtc tgaggcggat gccagcaccc caggccccac ccactcttgg          1520
Gln Ile Arg Val
            365 gggccaggat ccacctgctg gaaccagcct tatgcatggg gaaggcgggg ctggtgacaa    1580
ggcagggcaa gaggctgcag aagagtgtg ttccagctca gcccccaag ctgctctcgc     1640
tcccactgag ccaagccccc taactttggg cctagaggcc gttagtattt tatttggagt   1700
ttttaactct acaactgaag tttaaggtat ttggggaaaa cttagtccaa atggatctgc   1760
tgatggtggg aaggccagtg cttaacaaat ccatgtgtca tggggccagg tgagggaaac   1820
tgctggttct gctggtgcct ctgcccctgg cttctctctg ggagttgggt gcatcttatc   1880
agtgggaaat ctcccagcct taccaggcct gtgatggggg gtgggggtgg ggtggagatg   1940
tttctccagt tctgcctgcc ctggcagaat cttgacccag ggaaagggaa gcagggtagg   2000
agtccttctg agaaaggtct gtgtagccca ttaaccagga gcttggcaca ggccacatct   2060
gccccaagag catgagctcg tggctcagga gagccttcag gcccttgagg ccccccatggg  2120
cagtgctgtg tgggcagagg aggggtgata tgagagcgag cccagggaag gacctctggg   2180
caaaaagttc ccaggcccta actgcgtcta cttgctcagt cccagctctg cctgttgctc   2240
tagcccacag gctccctgcg gagggtctgg gcttggcgga ggacccagaa tggcactgag   2300
gccagcatgc tgtgggagt tgagcaaacc ctgggtgcca gtccaggagc tgtggctgga   2360
catgggtga tggggcggga tgcttgggcc tgggtctctc cgccagcagt gccaggagcc    2420
cttgctgggg aaatcaagac cagactagga tgcttctgcc ccaggcctgc cttccattct   2480
ttaacagccc atcttggctt ggggttgcaa tgatggctgg gccagtcact tgtggcaggg   2540
catcagggcc ctggcaggga agaacctagg cacctgggt tgtccccagc ctgcccgtca    2600
gcatgagata cccagtggga aagtgagagg atgcggagag gttggcagag ccaggggtag   2660
gttctggagg ctcaagcaac aaggaggtgc aggtaaaggg tgcagtgcag ccactgaggg   2720
acagctggga actgggggat gcaagtgaga aagggatgtg ggggagagtt caggatcagg   2780
ctgcttgagg agtaatgggt tacctacagc agagacgaga tggctgtttg tcaggaggcg   2840
gtagaaaggt agaaaggatt cagattgtgg aagggtaaat ggatgagatg accattaagg   2900
```

```
ttttgtttta ctgagaggct gtaagtctgc cagggacagc tgtcagtaag gctgcagaag    2960
ggctgggggg ctacacaagg aagagcagaa ctagggttgt aagctcaaat gacgagcaaa    3020
cggtgagaag gaggcctgaa gggctgtgtg gggactatgg ctacctgaag agggcacacc    3080
ctgttaaagg ggccacagct gctcagctgt tcttacagtg ccggccctgt gttgccagat    3140
tgtctgcttt gtcagaggcc agaattctga cttttatgt gaaataggat ttttaaatgc      3200
tggtgatcac ttaaaaaaaa cttaaaaacc caatactggc aaaagaggat gccagtttgc    3260
aatccctgaa gtagagagag ctcgtgctgg ggagaagtcc accaagatgc tttgaggcgg    3320
gctgtagcaa agtcctgttt ctcagagctg gctgggctg gggtaggatc cttgcagctg     3380
aggaggagga aaagccactg agtctcctcc cagagcggga caaaccagag gcccctttgca   3440 gttgctgggt caccagcggg ggtggcgcat ggagtacaga cagtgtagct cttggcctgc    3500
cagggagacg gatggtgcct ttgaagcaaa aggaaggga aggcagaacc agggatgcct     3560
ttgctgatga gagtgcctgt cagggaaggc gccacaggct ggcagctctt caaaccagca    3620
gcgcttgacc cagagccaga tccagcatgg cctggccaga ggcaccctgg gaggccagct    3680
ggtcagtccc ttgcctcccc aagttcccc tggggtcaat gagccctggg aggatgccta     3740
acctaactcc agccagacta ataggggcat ggtgacccct tgactcaccat cccatcccag   3800 cttttcaggga gtggggtag tgtggtctcc atgttcctac tatgcctaag aagagatggc    3860
tcaccttggg aggtgccagg ctgaaactag gtcctttccg ggtctggatg ctgccgctca    3920
ggagcagggg cgtggcctca gctgcctctg ggagcttccc gggaatgaca gggtttgagg    3980
ggagtagata tgagagggag ccgctcctgg ttctggagtc ttaggaggtt ccaacttgca    4040
ggatcctttc ccagagccct ccatggagaa aacagcaaaa tgaagccctt acctgcttgc    4100
tgtctgcaag ggagggagcc gagccccagc tgataatccc ccagcactca cccttcctga    4160
gctgagactt cggggctgtg gagaccagca caggacatag tggtgctttt taaatttatt    4220
tttaactgtt tctcatatgt agcaacccct cctcccctcc tgggcatgtt tacacaggct    4280
ctgctctggg ggctggcctg gctgtgaggt ttctgggggag gcagagaggc agggactttg    4340
gggccttagt caccatccat ggtatcacct catctcactt cctgtgaggg acagggcctg    4400
gctgatgtga tcccagctcc ccccagttca ggactgtctt tcagctcctt gccccctgga    4460
ggtgggggct gctggctgag gagggtcaa ggtgagttca agaaagctac ctgtggaaaa     4520
tggaccaggt tggggggtg attgcaaagt ctccccaaag cctggctcct catgctcagt     4580
gccaggggca gaacactggg gagccaggta tagagagcct tcctgtcata actgccagtc    4640
ctcttcctcc aaggcctctg catattctca tgttcccctc acccatcatg ccagccaccc    4700
ctatccctct tctagcaggg ccaagatggg gacagcagca gccctctggc cttgggatgt    4760
gatgataaag caagcctagg gccagggttt ggggagcaga gagagccaag aagttgacca    4820
cgtgtgattt ccagcccttc ccactgggac ttgacttccc aggtcaagga gtccgtctca    4880
ttctggctgg tcgagtgacc agaggcctgt gtgaatgtgt gcacctgctt ttcctgcctg    4940
gaatgttttc tggctcagct gcagcaacat ctgtgagccc agtgtctgcc ctgtgtccct    5000
gggctcgctc caagtgcagg aacatacatg cagggcccaa catgatgatg gtgtgaaggg    5060
caggaaacag tcctctgaag gagtggggag gtgggcagtc tgcccccgcc aggtaccatc    5120
gcctcctgcc agcttcctta gaccaggcag ggctgccatg gtgctagctg caagtccatc    5180
agtattgacc gtctcgctcc atcttggtcc tccggagtcc caagtttcct tttcatcaaa    5240
tctgacaaga gagaagaaac atgggtgtgc ttggcccaca gggcctggtg gtgatggacc    5300
```

```
tccccgctcc ctcaagctct ggatggctgc agtgttgtac tagactttgt tcaggctgtt    5360
ctcatctcag tattgcccct tcctttcact ttcacacttc atctcattcc tgttgtcact    5420
ttccccgaaa cgaataaagt ctccccagct cctgctgtgt aggctgggca gaaaccacaa    5480
c                                                                    5481
```

<210> SEQ ID NO 2
<211> LENGTH: 365
<212> TYPE: PRT
<213> ORGANISM: Homo sapiens

<400> SEQUENCE: 2

```
Met Pro Gly Gly Lys Lys Val Ala Gly Gly Ser Ser Gly Ala Thr
 1               5                  10                  15

Pro Thr Ser Ala Ala Ala Thr Ala Pro Ser Gly Val Arg Arg Leu Glu
            20                  25                  30

Thr Ser Glu Gly Thr Ser Ala Gln Arg Asp Glu Glu Pro Glu Glu Glu
        35                  40                  45

Gly Glu Glu Asp Leu Arg Asp Gly Gly Val Pro Phe Phe Val Asn Arg
    50                  55                  60

Gly Gly Leu Pro Val Asp Glu Ala Thr Trp Glu Arg Met Trp Lys His
65                  70                  75                  80

Val Ala Lys Ile His Pro Asp Gly Glu Lys Val Ala Gln Arg Ile Arg
                85                  90                  95

Gly Ala Thr Asp Leu Pro Lys Ile Pro Ile Pro Ser Val Pro Thr Phe
            100                 105                 110

Gln Pro Ser Thr Pro Val Pro Glu Arg Leu Glu Ala Val Gln Arg Tyr
        115                 120                 125

Ile Arg Glu Leu Gln Tyr Asn His Thr Gly Thr Gln Phe Phe Glu Ile
    130                 135                 140

Lys Lys Ser Arg Pro Leu Thr Gly Leu Met Asp Leu Ala Lys Glu Met
145                 150                 155                 160

Thr Lys Glu Ala Leu Pro Ile Lys Cys Leu Glu Ala Val Ile Leu Gly
                165                 170                 175

Ile Tyr Leu Thr Asn Ser Met Pro Thr Leu Glu Arg Phe Pro Ile Ser
            180                 185                 190

Phe Lys Thr Tyr Phe Ser Gly Asn Tyr Phe Arg His Ile Val Leu Gly
        195                 200                 205

Val Asn Phe Ala Gly Arg Tyr Gly Ala Leu Gly Met Ser Arg Arg Glu
    210                 215                 220

Asp Leu Met Tyr Lys Pro Pro Ala Phe Arg Thr Leu Ser Glu Leu Val
225                 230                 235                 240

Leu Asp Phe Glu Ala Ala Tyr Gly Arg Cys Trp His Val Leu Lys Lys
                245                 250                 255

Val Lys Leu Gly Gln Ser Val Ser His Asp Pro His Ser Val Glu Gln
            260                 265                 270

Ile Glu Trp Lys His Ser Val Leu Asp Val Glu Arg Leu Gly Arg Asp
        275                 280                 285

Asp Phe Arg Lys Glu Leu Glu Arg His Ala Arg Asp Met Arg Leu Lys
    290                 295                 300

Ile Gly Lys Gly Thr Gly Pro Ser Pro Thr Lys Ala Arg Lys Lys
305                 310                 315                 320

Asp Val Ser Ser Pro Gln Arg Ala Gln Ser Ser Pro His Arg Arg Asn
                325                 330                 335

Ser Arg Ser Glu Arg Arg Pro Ser Gly Asp Lys Lys Thr Ser Glu Pro
```

```
                    340                345                350
Lys Ala Met Pro Asp Leu Asn Gly Tyr Gln Ile Arg Val
         355                360                365

<210> SEQ ID NO 3
<211> LENGTH: 1945
<212> TYPE: DNA
<213> ORGANISM: Artificial Sequence
<220> FEATURE:
<223> OTHER INFORMATION: Description of Artificial Sequence: Synthetic
      polynucleotide derived from Homo sapien mRNA
<300> PUBLICATION INFORMATION:
<301> AUTHORS: Andersson, Bjorn
<302> TITLE: A 'double adaptor' method for improved shotgun library
      construction
<303> JOURNAL: Anal. Biochem.
<304> VOLUME: 236
<305> ISSUE: 1
<306> PAGES: 107-113
<307> DATE: 1998-04-02
<308> DATABASE ACCESSION NUMBER: Genebank/AF055021
<309> DATABASE ENTRY DATE: 1998-04-02

<400> SEQUENCE: 3
ctttgctgat gagagtgcct gtcagggaag gcgccacagg ctggcagctc ttcaaaccag       60
cagcgcttga cccagagcca gatccagcat ggcctggcca gaggcaccct gggaggccag      120
ctggtcagtc ccttgcctcc ccaagttccc cctggggtca atgagccctg gaggatgcc       180 taacctaact ccagccagac taatagggc atggtgaccc ttgactcacc atcccatccc       240
agctttcagg gagtggggt agtgtggtct ccatgttcct actatgccta agaagagatg       300
gctcaccttg gaggtgcca ggctgaaact aggtcctttc cgggtctgga tgctgccgct       360
caggagcagg ggcgtggcct cagctgcctc tgggagcttc ccgggaatga cagggtttga      420
ggggagtaga tatgagaggg agccgctcct ggttctggag tcttaggagg ttccaacttg      480
caggatcctt tcccagagcc ctccatggag aaaacagcaa aatgaagccc ttacctgctt      540
gctgtctgca agggagggag ccgagcccca gctgataatc ccccagcact caccccttcct     600 gagctgagac ttcggggctg tggagaccag cacaggacat agtggtgctt tttaaattta     660 ttttttaactg tttctcatat gtagcaaccc ctcctccct cctgggcatg tttacacagg      720
ctctgctctg ggggctggcc tggctgtgag gtttctgggg aggcagagag gcagggactt     780
tggggcctta gtcaccatcc atggtatcac ctcatctcac ttcctgtgag ggacagggcc     840
tggctgatgt gattccagct cccccccagtt caggactgtc tttcagctcc tttgcccctg    900
gaggtggggg ctgctggctg aggagggtc aaggtgagtt caagaaagct acctgtggaa      960
aatggaccag gttgggggg tgattgcaaa gtctccccaa agcctggctc ctcatgctca     1020
gtgccagggg cagaacactg gggagccagg tatagagagc cttcctgtca taactgccag     1080
tcctcttcct ccaaggcctc tgcatattct catgttcccc tcaccatca tgccagccac      1140 ccctatccct cttctagcag ggccaagatg gggacagcag cagccctctg gccttgggat    1200
gtgatgataa agcaagccta gggccagggt ttggggagca gagagagcca agaagttgac    1260
cacgtgtgat ttccagccct tcccactggg acttgacttc ccaggtcaag gagtccgtct    1320
cattctggct ggtcgagtga ccagaggcct gtgtgaatgt gtgcacctgc ttttcctgcc    1380
tggaatgttt tctggctcag ctgcagcaac atctgtgagc ccagtgtctg ccctgtgtcc    1440
ctgggctcgc tccaagtgca ggaacataca tgcagggccc aacatgatga tggtgtgaag   1500
ggcaggaaac agtcctctga aggagtgggg aggtgggcag tctgccccg ccaggtacca    1560 tcgcctcctg ccagcttcct tagaccaggc agggctgcca tggtgctagc tgcaagtcca   1620
```

```
tcagtattga ccgtctcgct ccatcttggt cctccggagt cccaagtttc cttttcatca    1680
aatctgacaa gagagaagaa acatgggtgt gcttggccca cagggcctgg tggtgatgga    1740 cctcccccgct ccctcaagct ctggatggct gcagtgttgt actagactt gttcaggctg    1800 ttctcatctc agtattgccc cttcctttca ctttcacact tcatctcatt cctgttgtca    1860 cttccccga aacgaataaa gtctccccag ctcctgctgt gtaggctggg cagaaaccac    1920
aaaaaaaaaa aaaaaaaaa aaaaa                                           1945
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide sense primer

<400> SEQUENCE: 4

```
gttcaggact gtctttcagc                                                  20
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide anti-sense primer

<400> SEQUENCE: 5

```
gtcaatactg atggacttgc                                                  20
```

<210> SEQ ID NO 6
<211> LENGTH: 764
<212> TYPE: DNA
<213> ORGANISM: Artificial Sequence
<220> FEATURE:
<223> OTHER INFORMATION: Description of Artificial Sequence: fragmented
      cDNA derived from Homo sapiens
<300> PUBLICATION INFORMATION:
<301> AUTHORS: Andersson, Bjorn
<302> TITLE: A 'double adaptor' method for improved shotgun library
      construction
<303> JOURNAL: Anal. Biochem.
<304> VOLUME: 236
<305> ISSUE: 1
<306> PAGES: 107-113
<307> DATE: 1998-04-02
<308> DATABASE ACCESSION NUMBER: Genebank/AF055021
<309> DATABASE ENTRY DATE: 1998-04-02

<400> SEQUENCE: 6

```
gttcaggact gtctttcagc tcctttgccc ctggaggtgg gggctgctgg ctgaggaggg      60
gtcaaggtga gttcaagaaa gctacctgtg gaaaatggac caggttgggg gggtgattgc     120
aaagtctccc caaagcctgg ctcctcatgc tcagtgccag gggcagaaca ctgggagcc      180 aggtatagag agccttcctg tcataactgc cagtcctctt cctccaaggc ctctgcatat     240
tctcatgttc ccctcaccca tcatgccagc accccctatc cctcttctag cagggccaag     300
atggggacag cagcagccct ctggccttgg gatgtgatga taaagcaagc ctagggccag     360
ggtttgggga gcagagagag ccaagaagtt gaccacgtgt gatttccagc ccttcccact     420
gggacttgac ttcccaggtc aaggagtccg tctcattctg gctggtcgag tgaccagagg     480
cctgtgtgaa tgtgtgcacc tgcttttcct gcctggaatg ttttctggct cagctgcagc     540
aacatctgtg agcccagtgt ctgccctgtg tccctgggct cgctccaagt gcaggaacat     600
```

-continued

```
acatgcaggg cccaacatga tgatggtgtg aagggcagga aacagtcctc tgaaggagtg    660
gggaggtggg cagtctgccc ccgccaggta ccatcgcctc ctgccagctt ccttagacca    720
ggcagggctg ccatggtgct agctgcaagt ccatcagtat tgac                    764
```

```
<210> SEQ ID NO 7
<211> LENGTH: 290
<212> TYPE: PRT
<213> ORGANISM: Homo sapiens

<400> SEQUENCE: 7

Met Trp Met His Val Ala Lys Val His Pro Lys Gly Gly Glu Met Val
1               5                   10                  15

Gly Ala Ile Arg Asn Ala Ala Phe Leu Ala Lys Pro Ser Ile Pro Gln
            20                  25                  30

Val Pro Asn Tyr Arg Leu Ser Met Thr Ile Pro Asp Trp Leu Gln Ala
        35                  40                  45

Ile Gln Asn Tyr Met Lys Thr Leu Gln Tyr Asn His Thr Gly Thr Gln
    50                  55                  60

Phe Phe Glu Ile Arg Lys Met Arg Pro Leu Ser Gly Leu Met Glu Thr
65                  70                  75                  80

Ala Lys Glu Met Thr Arg Glu Ser Leu Pro Ile Lys Cys Leu Glu Ala
                85                  90                  95

Val Ile Leu Gly Ile Tyr Leu Thr Asn Gly Gln Pro Ser Ile Glu Arg
            100                 105                 110

Phe Pro Ile Ser Phe Lys Thr Tyr Phe Ser Gly Asn Tyr Phe His His
        115                 120                 125

Val Val Leu Gly Ile Tyr Cys Asn Gly Arg Tyr Gly Ser Leu Gly Met
    130                 135                 140

Ser Arg Arg Ala Glu Leu Met Asp Lys Pro Leu Thr Phe Arg Thr Leu
145                 150                 155                 160

Ser Asp Leu Ile Phe Asp Phe Glu Asp Ser Tyr Lys Lys Tyr Leu His
                165                 170                 175

Thr Val Lys Lys Val Lys Ile Gly Leu Tyr Val Pro His Glu Pro His
            180                 185                 190

Ser Phe Gln Pro Ile Glu Trp Lys Gln Leu Val Leu Asn Val Ser Lys
        195                 200                 205

Met Leu Arg Ala Asp Ile Arg Lys Glu Leu Glu Lys Tyr Ala Arg Asp
    210                 215                 220

Met Arg Met Lys Ile Leu Lys Pro Ala Ser Ala His Ser Pro Thr Gln
225                 230                 235                 240

Val Arg Ser Arg Gly Lys Ser Leu Ser Pro Arg Arg Gln Ala Ser
                245                 250                 255

Pro Pro Arg Arg Leu Gly Arg Arg Glu Lys Ser Pro Ala Leu Pro Glu
            260                 265                 270

Lys Lys Val Ala Asp Leu Ser Thr Leu Asn Glu Val Gly Tyr Gln Ile
        275                 280                 285

Arg Ile
    290
```

POLYPEPTIDE AND DNA THEREOF USEFUL AS A NEOVASCULAR MARKER

This application is a Divisional of application Ser. No. 10/476,985 filed on Jan. 28, 2005 now abandoned, and for which priority is claimed under 35 U.S.C. §120. application Ser. No. 10/476,985 is the national phase of PCT International Application No. PCT/PCT/JP02/04251 filed on Apr. 26, 2002 under 35 U.S.C. §371. The entire contents of each of the above-identified applications are hereby incorporated by reference. This application also claims priority of Application No. 2001-136179 filed in Japan on May 7, 2001 under 35 U.S.C. §119.

TECHNICAL FIELD

The present invention relates to a polypeptide and a polynucleotide useful as a marker for neovascularization, vascular disease, inflammatory disease, entoptic neovascular disease, reproductive system disease, central nervous system disease or cancer. And the present invention relates to the treatment of those diseases.

BACKGROUND ART

By a double adapter method, a shotgun library of the human genome was constructed and a nucleotide sequence of AF055021 (SEQ ID NO: 3), EST clone, was determined with the DNA library (ANALYTICAL BIOCHEMISTRY, 236, 107-113 (1996).). Subsequently, a nucleotide sequence of full-length cDNA of AF055021 (SEQ ID NO: 1) was determined and named KIAA1036 (DNA Research, 6(3) 197-205 (1999).). KIAA1036 polypeptide (SEQ ID NO: 2) is a polypeptide consisting of 365 amino acids and the function has not been elucidated yet.

Since cells need oxygen and nutriments provided from blood to survive in vivo, neovascularization is vigorous in vigorously propagating tissues. It is known that neovascularization relates not only to the physiological regeneration of tissues but also to diseases accompanied by the pathological cell propagation. As the disease, vascular disease, inflammatory disease, entoptic neovascular disease, reproductive system disease, central nervous system disease and cancer were reported (Nature, 407, 249 (2000).). Since neovascularization is also observed upon the propagation of malignant neoplasma cell, human umbilical vein endothelial cells (HUVEC) treated with vascular endothelial cell growth factor (VEGF) were reported as a model of neovascularization caused by cancer (Cancer Research, 55, 5296☐5301 (1995).).

Though the research of genes relating to the above-mentioned various diseases have been conducted, the mechanism of pathogenesis has not been perfectly elucidated, there being a possibility of unknown genes relating to the mechanism. Under this circumstance, an identification of a new gene relating to the pathogenesis of the above-mentioned diseases and a diagnostic procedure of diseases with the gene have been desired.

DISCLOSURE OF INVENTION

The present inventors found that expression of KIAA1036 polypeptide was increased in ovarian cancer and colon cancer and confirmed that the peptide was useful as a marker for cancer. As results of further researches, they found that KIAA1036 polypeptide was a new marker for neovascular and useful as a marker and a therapeutic agent of various diseases such as vascular disease relating to neovascularization, inflammatory disease, entoptic neovascular disease, reproductive system disease, central nervous system disease or cancer to accomplish the present invention.

The present invention is (1) a marker for neovascularization, vascular disease, inflammatory disease, entoptic neovascular disease, reproductive system disease, central nervous system disease or cancer, which contains a polynucleotide having a base sequence as set forth in A of 386-C of 1480 of SEQ ID NO: 1 or fragment thereof, (2) a marker for neovascularization, vascular disease, inflammatory disease, entoptic neovascular disease, reproductive system disease, central nervous system disease or cancer, which contains a polynucleotide hybridizing under a stringent condition with a polynucleotide having a base sequence as set forth in C of 1-C of 1480 of SEQ ID NO: 1 or fragment thereof, (3) a marker of (1), which contains a polynucleotide having a base sequence as set forth in C of 1-C of 1480 of SEQ ID NO: 1 or fragment thereof, (4) a marker of (1), which contains a polynucleotide having a base sequence as set forth in C of 1-C of 5481 of SEQ ID NO: 1 or fragment thereof, (5) a marker for neovascuarlization, vascular disease, inflammatory disease, entoptic neovascular disease, reproductive system disease, central nervous system disease or cancer, which contains a polypeptide comprising an amino acid sequence as set forth in Met of 1-Val of 365 of SEQ ID NO: 2 or fragment thereof, (6) a marker for neovascularization, vascular disease, inflammatory disease, entoptic neovascular disease, reproductive system disease, central nervous system disease or cancer, which contains a polypeptide wherein 1 or more amino acid residue(s) has a mutation(s) selected from deletion, substitution and addition in an amino acid sequence as set forth in Met of 1-Val of 365 of SEQ ID NO: 2 or fragment thereof, (7) a marker of (5), which contains a polypeptide comprising an amino acid sequence as set forth in Met of 1-Val of 365 of SEQ ID NO: 2 or fragment thereof, (8) a method of detection of a marker of any one of (1)-(7) from a sample derived from human, (9) a method of detection or assay of a marker of any one of (1)-(4), which comprises the following processes and using a polynucleotide having a base sequence as set forth in A of 386-C of 1480 of SEQ ID NO: 1 or fragment thereof, (a) a process that the polynucleotide and a sample are contacted, and (b) a process that a polynucleotide binding with the polynucleotide is detected,

(10) a method of detection or assay of a marker of any one of (1)-(4), which comprises the following processes and using a polynucleotide having a base sequence as set forth in A of 386-C of 1480 of SEQ ID NO: 1 or fragment thereof, (a) a process that cDNA is prepared from a sample, and (b) a process that cDNA is amplified with the polynucleotide fragment and detected,

(11) a method of detection or assay of a marker of any one of (5)-(7), which comprises the following processes and using an antibody recognizing a polypeptide comprising an amino acid sequence as set forth in Met of 1-Val of 365 of SEQ ID NO: 2 or fragment thereof, (a) a process that the antibody and a sample are contacted, and (b) a process that the binding between the antibody and a polypeptide is detected, (12) a method of detection of a disease relating to a marker of any one of (1)-(7), which comprises using a method of any one of (9)-(11),

(13) a method of detection of (12), wherein the disease is vascular disease, inflammatory disease, entoptic neovascular disease, reproductive system disease, central nervous system disease or cancer,

(14) a diagnostic kit of a disease relating to a marker of any one of (1)-(7), which comprises using a method of any one of (9)-(11),

(15) a diagnostic kit of (14), wherein the disease is vascular disease, inflammatory disease, entoptic neovascular disease, reproductive system disease, central nervous system disease or cancer,

(16) a screening method of a binding substance of a marker of any one of (5)-(7), which comprises the following processes,
(a) a process that a marker of any one of (5)-(7) and a subject are contacted, and
(b) a process that the binding between the marker and the subject is detected,

(17) a kit for screening of a binding substance of (16), which contains a polypeptide comprising an amino acid sequence as set forth in SEQ ID NO: 2 or fragment thereof,

(18) a screening method of a binding activity regulatory substance which regulates a binding between a marker of any one of (5)-(7) and a binding substance of the marker, which comprises the following processes,
(a) a process that a marker of any one of (5)-(7) and a binding substance of the marker are contacted in the presence or absence of a subject, and
(b) a process that a binding activity of the marker and the binding substance is compared in the presence or absence of a subject,

(19) a kit for screening of a binding activity regulatory substance of (18), which contains a polypeptide comprising an amino acid sequence as set forth in SEQ ID NO: 2 or fragment thereof,

(20) a screening method of an expression regulatory substance of a marker of any one of (1)-(7), which comprises the following processes,
(a) a process that a cell, which can express a marker of any one of (1)-(7), and a subject are contacted, and
(b) a process that a change of an expression level of the marker is detected by using a method of any one of (9)-(11),

(21) a kit for screening of an expression regulatory substance of a marker of any one of (1)-(7), which comprises using the method of (20),

(22) a DNA synthesis inhibitor containing a polypeptide comprising an amino acid sequence as set forth in Met of 1-Val of 365 of SEQ ID NO: 2 or fragment thereof,

(23) a cell migrating activity inhibitor containing a polypeptide comprising an amino acid sequence as set forth in Met of 1-Val of 365 of SEQ ID NO: 2 or fragment thereof,

(24) a pharmaceutical composition which contains at least one selected from a DNA synthesis inhibitor of (22), a cell migrating activity inhibitor of (23), a polynucleotide having a base sequence as set forth in SEQ ID NO: 1 or fragment thereof, a human gene therapeutic expression vector containing polynucleotide having a base sequence as set forth in SEQ ID NO: 1 or fragment thereof, a polypeptide comprising an amino acid sequence as set forth in SEQ ID NO: 2 or fragment thereof and an antibody to the polypeptide,

(25) a pharmaceutical composition of (24), which is a therapeutic agent for vascular disease, inflammatory disease, entoptic neovascular disease, reproductive system disease, central nervous system disease or cancer,

(26) a method of treating vascular disease, inflammatory disease, entoptic neovascular disease, reproductive system disease, central nervous system disease or cancer, which comprises administrating a pharmaceutical composition of (24) or (25),

(27) use of a polynucleotide having a base sequence as set forth in SEQ ID NO: 1 and a polypeptide comprising an amino acid sequence as set forth in SEQ ID NO: 2 to produce a pharmaceutical composition of (24) or (25).

BRIEF DESCRIPTION OF THE DRAWINGS

FIG. 1 is a schematic comparing an amino acid sequence of KIAA1036 and that of AK022567.
Query: 614 shows an amino acid sequence of KIAA1036.
Sbjct: 1 shows an amino acid sequence of AK022567.
FIG. 3 shows an expression level of KIAA1036 in human cancer tissues by Dot blot.
By using a nylon membrane on which cDNA was immobilized, wherein cDNA was derived from a cancer tissue obtained from a patient with human ovarian cancer or large bowel cancer and a normal tissue obtained from the same patient, signal intensity of KIAA1036 gene against signal intensity of β-actin gene was calculated. The ratio of signal intensity in each cancer tissue against in each normal tissue of the same patient was calculated. And a change of expression level of the gene in each cancer tissue was analyzed. As a result, in cancer tissue of all of the 4 patients with ovarian cancer and all of the 11 patients with large bowel cancer, the expression of KIAA1036 gene was increased.

Figure 2:
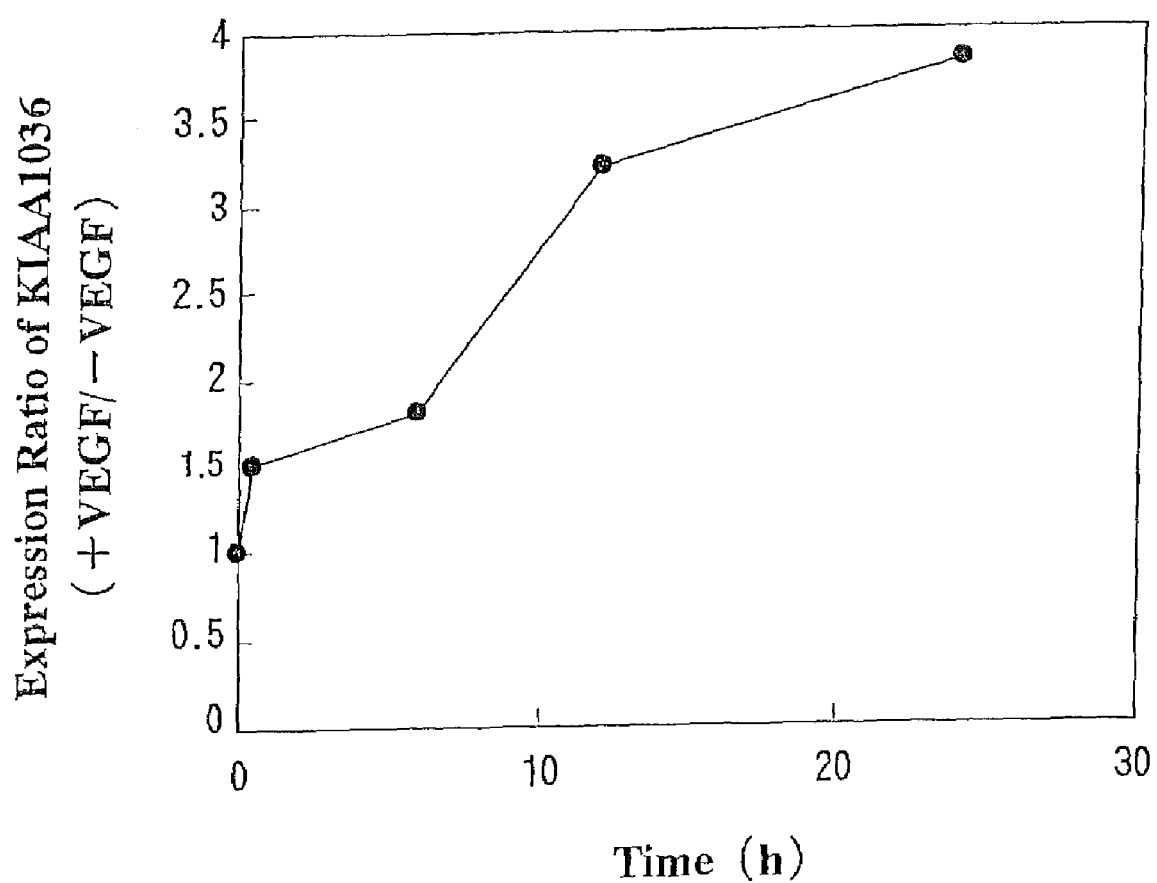
FIG. 2 shows an expression level of KIAA1036 in human umbilical vein endothelial cells by Northern blot.
Total RNA was prepared by treating human umbilical vein endothelial cell with 1 nM VEGF for 0, 0.5, 2, 6, 12 or 24 hours. And then signal intensity of KIAA1036 gene against signal intensity of β-actin gene was calculated. A relative expression level is shown when signal intensity in a control division (1 nM VEGF was not added) is 1.
The expression was inhibited in 0.5 to 2 hours after VEGF was added. But a 3.2-fold high gene expression was induced at 24 hours after VEGF was added.

As a result, regardless of the addition of VEGF, migrating activity of cells was inhibited, depending on the concentration of added KIAA1036 polypeptide.

BEST MODE FOR CARRYING OUT THE INVENTION

Preparation of KIAA1036 polynucleotide which is a marker of the present invention, preparation of the polypeptide, a recombinant vector, a transformant, a method of production thereof, an antibody, the method of detection of polypeptide, a method of detection of mRNA, the method of detection of neovascularization, vascular disease, inflammatory disease, entoptic neovascular disease, reproductive system disease, central nervous system disease or cancer and a diagnostic kit, a therapeutic agent or a method of treating for vascular disease, inflammatory disease, entoptic neovascular disease, reproductive system disease, central nervous system disease or cancer are explained below. In this description, if there is no instruction, a gene recombinant technique, a production engineering technique of a recombinant polypeptide in animal cells, insect cells, yeast and *Escherichia coli*, a molecular-biological method, the method of separation and purification of expressed polypeptide, assay and immunological method, which are well-known in this field, are adopted.

A marker of the present invention is "a polynucleotide having a base sequence as set forth in A of 386-C of 1480 of SEQ ID NO: 1 or fragment thereof" and a polynucleotide sequence of KIAA1036. Additionally, a marker of the present invention includes "a polynucleotide having a base sequence as set forth in C of 1-C of 1480 of SEQ ID NO: 1 or fragment thereof" and "a polynucleotide hybridizing with the present invention marker under a stringent condition or fragment thereof". Hereinafter, a polynucleotide, which is a marker of the present invention, is referred to as polynucleotide A.

In this description, "neovascularization" means a phenomenon that a new vasculature is developed from an existing vasculature. A disease related to "neovascular" includes "vascular disease", "inflammatory disease", "entoptic neovascular disease", "reproductive system disease", "central nervous system disease" or "cancer".

"Vascular disease" includes arterial sclerosis, hypertonia, angina pectoris, obstructive arteriosclerosis, myocardial infarction, cerebral infarction, diabetic angiopathy or vascular malformation. "Inflammatory disease" includes hepatitis, pneumonitis, glomerular nephritis, thyreoiditis, osteitis, arthromeningitis, osteoclasia, chondrolysis, rheumatism, bronchial asthma, sarcoidosis, Crow-Fukase syndrome, pannus, allergic oedema, ulcers, hydroperitoneum, peritoneal screlosis or tissular conglutination. "Entoptic neovascular disease" includes diabetic retinopathy, occlusion of retinal vein or aging macular degeneration. "Reproductive system disease" inlcudes uterus dysfunction, placental dysfunction, ovarian hyperergasia or follicle cyst. "Central nervous system disease" includes retinosis, cerebral apoplexy, vascular dementia or Alzheimer disease. "Cancer" includes a malignant neoplasma such as solid cancer, angiomatous, hemangioendothelioma, sarcomas, sarcoma or hematopoietic organic ulcer, ovarian cancer or large bowel cancer. Additionally, it includes metastatics of these cancers.

"A polynucleotide hybridizing under a stringent condition" means a polynucleotide obtainable by a generally known and common method in this field with using a fragment of polynucleotide A as a probe, for example, colony hybridization, plaque hybridization or Southern blotting hybridization. An example of the above polynucleotide includes a polynucleotide obtained by hybridization at 65° C. in the presence of 0.7 to 1.0M NaCl by using a membrane on which polynucleotides from colony or plaque are immobilized and a washing of a membrane at 65° C. with SSC (Saline Sodium Citrate; 150 mM sodium chloride, 15 mM sodium citrate) solution whose concentration is 0.1-fold to twice. Hybridization can be performed as well as methods described in Molecular Cloning: A Laboratory Manual, Second Edition (1989)(Cold Spring Harbor Laboratory Press), Current Protocols in Molecular Biology (1994)(Wiley-Interscience), DNA Cloning 1: Core Techniques, A practical Approach, Second Edition (1995)(Oxford University Press). Preferably, sequences comprising of only adenine (a) or thymine (T) are excluded from sequences hybridizing under a stringent condition. "A fragment of a polynucleotide" includes a polynucleotide having a base sequence comprising 5 or more serial bases in a base sequence of SEQ ID NO: 1, for example, a polynucleotide having a base sequence comprising 5, 8, 10, 12, 15, 20, 25, 30, 50, 100, 500 or 1000 bases.

In this description, "a polynucleotide hybridizing" includes a polynucleotide hybridizing with the other polynucleotide under the above hybridizing condition. Examples of the above polynucleotide includes a polynucleotide having a homology of at least 60% or more, preferably 80% or more and more preferably 95% or more with a base sequence of DNA encoding a polypeptide having an amino acid sequence of SEQ ID NO: 1. And the homology is shown as a score, for example, by using a search program BLAST with algorithm developing by Altschul et al (The Journal of Molecular Biology, 215, 403-410 (1990).).

A marker of the present invention includes "a polypeptide comprising an amino acid sequence as set forth in Met of 1-Val of 365 of SEQ ID NO: 2 or fragment thereof", a polypeptide sequence of KIAA1036 including their salts. A "salt" includes a salt physiologically acceptable with an acid or a base. A salt with an acid is especially preferable. The salt includes, for example, a salt with inorganic acid such as hydrochloric acid, phosphoric acid, hydrobromic acid or sulfuric acid, or a salt with organic acid such as acetic acid, fomic acid, proprionic acid, fumaric acid, maleic acid, succinic acid, tartaric acid, citric acid, malic acid, oxalic acid, benzoic acid, methanesulfonic acid or benzenesulfonic acid. "A fragment of polypeptide" includes a polypeptide sequence comprising 5 or more serial amino acid residues in an amino acid sequence of SEQ ID NO: 2, for example, a polypeptide comprising an amino acid sequences comprising 5, 8, 10, 12, 15, 20, 25, 30, 50 or 100 amino acid residues.

A marker of the present invention includes "a polypeptide having a mutation selected from deletion, substitution and addition in 1 or a few amino acid residue(s) of an amino acid sequence as set forth in Met of 1-Val of 365 of SEQ ID NO: 2 or fragment thereof". Hereinafter, a polypeptide, which is a marker of the present invention, is referred to as polypeptide B.

"1 or a few amino acid residue(s)" means amino acid residues, which can delete, substitute or add by a site-specific mutagenic method or the like. Namely, it means amino acid residues having 50 or less, preferably 30 or less, more preferably 20 or less, much more preferably 10 or less amino acid residues. Furthermore, polypeptide B includes a polypeptide to be used as a marker for neovascularization, vascular disease, inflammatory disease, entoptic neovascular disease, reproductive system disease, central nervous system disease or cancer even after deletions, substitutions or additions. It is, for example, a polypeptide having a homology of at least 60% or more, preferably 80% or more and more preferably 95% or more with an amino acid sequence of SEQ ID NO: 2.

In this description, "a marker" includes a substance used to detect neovascularization and all kinds of disease related to neovascularization derived from organism samples, for example, vascular disease, inflammatory disease, entoptic neovascular disease, reproductive system disease, central nervous system disease or cancer. And it includes polynucleotide A and polypeptide B. mRNA or a protein can be a "marker" when the expression increases or decreases under diseases. Examples of the above maker include KIAA1036 polypeptide comprising an amino acid sequence as set forth in Met of 1-Val of 365 of SEQ ID NO: 2, KIAA1036 polynucleotide having a base sequence as set forth in A of 386-C of 1480 of SEQ ID NO: 1, a polynucleotide having a complementary base sequence thereof or a fragment thereof.

In this description, terms are used with usual meanings in this field unless otherwise mentioned especially referred. The terms especially used in this description are explained below.

An "antibody" means a general antibody in this field and includes all of the antibodies, fragments thereof, derivatives, conjugations or modified antibodies. An antibody recognizing polypeptide B or fragment thereof is preferable, an antibody recognizing specifically the above polypeptide is more preferable and an antibody recognizing single specifically the polypeptide is much more preferable. These antibodies include a polyclonal antibody or a monoclonal antibody.

"A detection or a quantitation" of a marker of the present invention can be accomplished by any appropriate method including an immunological assay or a molecular-biological assay.

When a marker is polypeptide B, the above method includes, for example, an immunological assay such as ELISA (Enzyme Linked Immuno Sorbent Assay), RIA (Radio Immuno Assay), fluorescence antibody technique, Western blot or an immune structure dyeing method.

By using an antibody against polypeptide B or fragment thereof, neovascularization, vascular disease, inflammatory disease, entoptic neovascular disease, reproductive system disease, central nervous system disease or cancer can be detected or quantitated. Because a marker of the present invention can be used as a marker for above diseases, a method of detection or quantitation of diseases with the above antibody can be accomplished by any appropriate method including an immunological assay as well as an above detection or quantitation of a polypeptide.

The present invention relates to a diagnostic kit of neovascularization, vascular disease, inflammatory disease, entoptic neovascular disease, reproductive system disease, central nervous system disease or cancer, characterized by including an antibody against polypeptide B or fragment thereof. The above kit includes at least an antibody against polypeptide B or fragment thereof and a standard reagent of polypeptide B. Because polypeptide B can be used as a marker for neovascularization, vascular disease, inflammatory disease, entoptic neovascular disease, reproductive system disease, central nervous system disease or cancer, it can be immunologically measured as well as an above mentioned method of detection or quantitation by an immunological assay.

And when a marker is a polynucleotide such as mRNA, the assay includes a molecular-biological assay, for example, Northern blot, Dot blot or polymerase chain reaction (PCR).

mRNA can be detected or quantitated by using polynucleotide A or fragment thereof as a probe or primer.

Because a marker of the present invention can be a marker of above diseases, a method of detection or quantitation of diseases with the probe or the primer is accomplished by an appropriate method including a molecular-biological assay as well as the above method for detection or quantitation of a polynucleotide.

A probe or a primer includes a nucleotide comprising serial bases in a base sequence of SEQ ID NO: 1, for example, a base sequence comprising 5, 8, 10, 12, 15, 20, 25, 30, 40, 50 or 60 bases. It includes an oligonucleotide having the same sequence, an oligonucleotide having a sequence complementary to the sequence of the oligonucleotide, and the derivative thereof. A derivative thereof includes, for example, a oligonucleotide wherein a phosphodiester bond in the oligonucleotide is transformed into a phosphorothioate bond or a N3'-P5' phosphoamidite bond, a oligonucleotide wherein a ribose and a phosphodiester bond are transformed into a peptide bond, a oligonucleotide wherein a uracil in the oligonucleotide is substituted with a C-5 propionyl uracil or a C-5 thiazole uracil, a oligonucleotide wherein a cytosine in the oligonucleotide is substituted with C-5 propionyl cytosine or cytosine modified with phenoxazine or a oligonucleotide wherein a ribose in DNA is substituted with 2'-O-propyl ribose, 2'-methoxyethoxy ribose or the like. Those polynucleotides are useful, for example, as a gene marker, a primer for PCR or a probe for hybridization.

The present invention relates to a part or all of the polynucleotide encoding polypeptide B and a diagnostic kit of vascular disease, inflammatory disease, entoptic neovascular disease, reproductive system disease, central nervous system disease or cancer including the polynucleotide as a standard reagent. This kit includes at least a probe or a primer against polynucleotide A or fragment thereof and a standard reagent of polynucleotide A. Because polynucleotide A can be used as a marker for neovascularization, vascular disease, inflammatory disease, entoptic neovascular disease, reproductive system disease, central nervous system disease or cancer, it is molecular-biologically measured as well as the above method of detection or quantitation by a molecular-biological assay.

A transcription of DNA or a translation of mRNA can be inhibited by using polynucleotide A. Methods to inhibit transcription of DNA or translation of mRNA of the polypeptide B can be provided by appropriately preparing a polynucleotide having a complementary base sequence to a base sequence of polynucleotide A, a polynucleotide hybridizing with polynucleotide A or an oligonucleotide and a derivative oligonucleotide having a complementary sequence to an oligonucleotide having serial 5 to 60 base sequences in base sequence of polynucleotide A and using antisense RNA/DNA techniques known in this field.

The present invention relates to "a screening method of a binding substance" of a marker of the present invention. "A binding substance" includes any substance binding to a marker of the present invention. The binding substance includes, for example, a low-molecular weight substance, a polynucleotide or a polypeptide such as a receptor and an antibody. "A screening method of a binding substance" can be accomplished by appropriately using techniques widely known in this technical field. It includes, for example, a bioassay and a binding assay.

"A kit for screening of a binding substance" of the present invention includes at least a marker of the present invention. A binding substance can be screened by biochemical method with the above kit.

Additionally the present invention relates to "a screening method of a binding activity regulatory substance". "A binding activity regulation" means that a binding activity of a marker of the present invention and the binding substance is enhanced or reduced and "a binding activity" is evaluated by Percent Maximum Binding (PMB). "A binding activity regulatory substance" includes a substance that makes a binding activity of the binding substance against a marker of the present invention enhanced or reduced, for example, an agonist or an antagonist. The substance includes, for example, a low-molecular weight substance, a polynucleotide or a polypeptide. "A screening method of a binding activity regulatory substance" can be accomplished by appropriately using techniques widely known in this field. A binding activity regulatory substance can be screened by a screening method of the present invention. The method is, for example, a bioassay or a binding assay.

"A screening kit of a binding activity regulatory substance" of the present invention includes at least a marker of the present invention. A binding activity regulatory substance can be screened by a biochemical method with a kit of the present invention.

And the present invention relates to "a screening method of an expression regulatory substance". Expression level means the amount of a marker of the present invention expressed in target cells. Expression level can be evaluated by an appropriate method including an immunological assay with an antibody against polypeptide B, for example, ELISA, RIA, a fluorescence antibody technique or an immune structure dyeing method or by a molecular-biological assay measuring mRNA of polynucleotide A, for example, Northern blot hybridization, Dot blot or RT-PCR. "Expression regulation" means that expression level of a marker of the present invention in protein or mRNA level evaluated by any appropriate method including the above immunological or molecular-biological assay is enhanced or reduced. "An expression regulatory substance" includes a substance enhancing or reducing expression level of a marker of the present invention in protein or mRNA level, which can be evaluated by any appropriate method including the above immunological or molecular-biological assay. The above substance includes, for example, a low-molecular weight substance, a polynucleotide or a polypeptide. "A screening method of an expression regulatory substance" can be accomplished by appropriately using techniques widely known in this field. An expression regulatory substance can be screened by a screening method of the present invention. The method includes, for example, a bioassay or a binding assay.

"A screening kit of an expression regulatory substance" of the present invention includes at least a marker of the present invention. An expression regulatory substance can be screened by a biochemical method based on a screening method of an expression regulatory substance with a kit of the present invention.

Because polypeptide B inhibits DNA synthesis in a vascular endothelial cell and a migrating activity of a vascular endothelial cell, polynucleotide A, a complementary polynucleotide of the above polynucleotide, polypeptide B or/and an antibody against the above polypeptide can be a DNA synthesis inhibitor or/and a cell migrating activity inhibitor. Then, the present invention provides a DNA synthesis inhibitor and a cell migrating activity inhibitor.

"A pharmaceutical composition" of the present invention includes at least one selected from polypeptide B, an antibody against the polypeptide, polynucleotide A, a complementary polynucleotide of the polynucleotide, a DNA synthesis inhibitor, a cell migrating activity inhibitor, a binding substance, a binding activity regulatory substance and an expression regulatory substance. It can be used for a therapeutic agent of a specific disease, for example, vascular disease, inflammatory disease, entoptic neovascular disease, reproductive system disease, central nervous system disease or cancer. The substance includes, for example, a low-molecular weight substance, a polynucleotide or a polypeptide. Preferred is a polypeptide comprising an amino acid sequence as set forth in Met of 1-Val of 365 of SEQ ID NO: 2 or fragment thereof. And a pharmaceutical composition of the present invention includes "a gene therapeutic expression vector". "A gene therapeutic expression vector" includes an expression vector inserted all or a part of polynucleotide A and a vector which inserts a normal gene in a cell, repairs/modifies a defect of a gene and regulates an expression of a gene by introducing a gene in a cell/tissue. The vector includes a viral vector wherein a part or all of a base sequence of a viral, which is lack of reproductive capability, is replaced with a therapeutic gene. Then, the present invention provides therapeutic agents or methods of treating for these diseases.

"A method of treating" includes a method for treating of specific diseases, for example, vascular disease, inflammatory disease, entoptic neovascular disease, reproductive system disease, central nervous system disease or cancer relating to neovascularization by a administration of the above pharmaceutical composition.

Hereinafter, the present invention is described in detail.

(1) An Preparation of KIAA1036 Polynucleotide cDNA library is manufactured from human brain, heart, skeletal muscle, spleen, kidney, liver, small intestine, placenta, human normal cells from these tissues, human umbilical vein endothelial cells or human ovarian cancer or human large bowel cancer by a usual method.

A method which manufactures cDNA library is a method described in Molecular Cloning: A Laboratory Manual, Second Edition (1989) (Cold Spring Harbor Laboratory Press), Current Protocols in Molecular Biology (1994) (Wiley-Interscience) or DNA Cloning 1: Core Techniques, A Practical Approach, Second Edition (1995) (Oxford University Press) or the method that a kit on the market, for example, SuperScript Plasmid System for cDNA Synthesis and Plasmid Cloning (Invitrogen) or ZAP-cDNA Synthesis Kits (STRATAGENE) is used.

cDNA obtained by the method is, for example, DNA encoding a polypeptide of SEQ ID NO: 2. Examples of the above cDNA include a DNA comprising a base sequence of SEQ ID NO: 1. A plasmid including DNA of SEQ ID NO: 1 is, for example, a plasmid described in the following examples.

The obtained DNA is inserted to an appropriate expression vector and an expression plasmid is constructed. The expression vectors are introduced to appropriate hosts and then transformants can be obtained. The expression vector is any vector in which cDNA is inserted and which express in animal cells. The vector is, for example, pcDNA1.1, pcDNA1.1/Amp, pCDM8, pREP (Invitrogen), pHM6, pHB6 (Roche Diagnostics), pKK223-3, pGEX (Amersham Pharmacia Bioteque), pET-3, pET-11, pBluescriptII SK(+), pBluescriptII SK(-) (STRATAGENE), pUC19, pTrxFus (Invitrogen), pUC118, pSTV28 (TaKaRa), pMAL-c2X (New England BioLabs), pAGE107 (Cytotechnology, 3(2), 133-140 (1990).; JP1991-22979), pAGE103 (The Journal of Biochemistry, 101(5), 1307-1310 (1987).), pAMo, pAMoA (The Journal of Biological Chemistry, 268(30), 22782-22787 (1993).), pAMoPRSA (JP1993-336963) or pAS3-3 (JP1990-227075).

The expression vectors with a cDNA insert introduce a target cDNA into optional animal cells and transformed cells are obtained. Any method for introducing DNA can be used as a method for introducing the expression vectors into a host. When a host is animal cells, it is, for example, an electroporation (Cytotechnology, 3(2), 133-140 (1990).), a calcium phosphate method (JP1990-227075) or a lipofection method (Proceedings of the National Academy of Sciences USA, 84, 7413 (1987).; Virology, 52, 456 (1973).).

Appropriate cells or tissue for expression vectors can be used as a host. It is, for example, animal cells. An animal cell as a host is, for example, Namalwa (Burkitt lymphoma, ATCC CRL-1432) and the subline NamalwaKJM-1 which is an established cell from human, HCT-15 (human large bowel cancer cell, ATCC:CCL-225), COS-1(African green monkey's nephrocyte (SV40 transformed cell), ATCC:CRL-1650) and COS-7(African green monkey's nephrocyte (SV40 transformed cell), ATCC:CRL-1651) which is an established cell from monkey or CHO-K1(Chinese hamster ovary cell, ATCC:CCL-61) and HBT5637(JP1987-299) which is an established cell derived from hamster. Preferred is Namalwa cell, NamalwaKJM-1 cell or HCT-15 cell.

Transformants of the present invention are cultured by a generally known and common method in this field. It can be accomplished with a medium appropriate to a transforming host and a liquid medium is appropriate as a medium for a culturing liquid medium. For example, MEM medium (Science, 130, 432 (1959).), D-MEM medium (Virology, 8, 396 (1959).), RPMI 1640 medium (The Journal of the American Medical Association, 199, 519 (1967).), YT medium or BEM medium can be used.

When transformants is prepared by using animal cells as a host are cultured, for example, a medium wherein cattle fetal serum (FCS) is appropriately added into MEM medium, D-MEM medium or PRIM medium can be used. A medium can optionally include a substance promoting transcription activity to enhance transcription activity of a promoter of an expression vector. For example, isopropyl-1-thio-β-D-galactopyranosin (IPTG) can be used.

A medium includes nutriments needed to grow up transformants, for example, glucose, amino acid, peptone, vitamin, hormone or serum, preferably, FCS, calcium chloride or magnesium chloride. The medium like this, which has any composition, can be used and a medium available on the market can be used. A cultivation is held in pH 6.0 to 8.0 at 25 to 40° C. in the presence of 5% $CO_2$.

The obtained transformed cells are cultured by a usual method. For example, they can be cultured by the following culture method. When transformants are animal cells, examples of a medium for culturing the cells includes commonly used RPMI1640 medium (The Journal of the American Medical Association, 199, 519 (1967).), MEM medium of Eagle (Science, 122, 501 (1952).), D-MEM medium (Virology, 8, 396 (1959).), 199 medium (Proceeding of the Society for the Biological Medicine, 73, 1(1950).) or a medium added fetal calf serum (FCS).

Cultivation is usually carried out in pH 6 to 8, at 25 to 40° C., in the presence of 5% $CO_2$ for 1 to 7 days. An antibiotic such as kanamycin, penicillin or streptomycin can optionally be added during cultivation.

DNAs encoding KIAA1036 which is a neovascular marker can be obtained from human brain, heart, skeletal muscle, spleen, kidney, liver, lung, placenta, human normal cells from these tissues, human umbilical vein endothelial cells or human ovarian cancer or human large bowel cancer by the above-mentioned.

On the basis of an amino acid sequence, DNA encoding KIAA1036 can be prepared by a chemical synthesis. A chemical synthesis of DNA can be accomplished with a DNA synthesizer using a thiophosphite method (Shimazu Corporation) or a DNA synthesizer model 392 using a phosphoamidite method (PerkinElmer, Inc.).

The following oligonucleotide is used as a sense primer (SEQ ID NO: 4) or an antisense primer (SEQ ID NO: 5) and cDNA prepared from mRNA in cells expressing complementary mRNA of these DNA is used as a template. Target DNA can be prepared by PCR under this condition.

(2) The Production of KIAA1036 Polypeptide

KIAA1036 can be produced by a method described in Molecular Cloning: A Laboratory Manual, Second Edition (1989) (Cold Spring Harbor Laboratory Press) or Current Protocols in Molecular Biology (1994) (Wiley-InterScience). For example, KIAA1036 polynucleotide is made to express in host cells by the following method and KIAA1036 can be produced.

On a basis of a full length of DNA encoding KIAA1036 polypeptide, an appropriate length of DNA fragment including a part encoding the polypeptide is optionally prepared. And DNA whose bases substituted is prepared, as a base sequence encoding the polypeptide is the most suitable codons for expression in a host. This DNA is useful to enhance productivity of the polypeptide. By inserting the DNA fragment or a full length of DNA to the downstream of a promoter of an appropriate expression vector, a recombinant DNA (a recombinant vector) is produced. By the recombinant vectors are produced in host cells adapting to the expression vector, transformants producing KIAA1036 polypeptide can be obtained.

Any cell such as a prokaryotic cell, yeast, an animal cell, a plant cell or a insect cell can be used as a host cell, if a target gene can be expressed in the cells. As an expression vector, the vector which can autonomously replicate in the above host cells or be inserted into a chromosome and which includes a promoter at the appropriate position for the transcription of KIAA1036 polypeptide gene can be used.

(i) The Case that Prokaryote is Used as a Host.

An expression vector of KIAA1036 can autonomously replicate in prokaryote as well as is preferably constructed with a promoter, a ribosome binding sequence, KIAA1036 and a transcription termination sequence. A gene regulating a promoter can be included.

An expression vector is, for example, pBTrp2, pBTac1, pBTac2 (Roche Diagnostics), BluescriptII SK(+), BluescriptII SK(−) (STRATAGENE), pSTV28, pUC118, pUC19 (TaKaRa), pKK233-2 (Pharmacia), pSE280, pSupex, pUB110, pTP5, pC194, pTrxFus (Invitrogen), pGEMEX-1 (Promega), pQE-8 (QIAGEN), pGEX (Pharmacia), pETsystem (Novagen), pMAL-c2 (New England BioLabs), pKYP10 (JP1982-110600), pKYP200 (Agricultural Biological Chemistry, 48, 669 (1984).), pLSA1 (Agricultural Biological Chemistry, 53, 277 (1989).), pGEL1 (Proceedings of the National Academy of Sciences USA, 82, 4306 (1985).), pEG400 (Journal of Bacteriology, 172, 2392 (1990).), pTrs30 (FERM BP-5407), pTrs32 (FERM BP-5408), pGHA2 (FERM BP-400), pGKA2 (FERM BP-6798), pPA1 (JP1987-233798) or pTerm2 (JP1990-22979, U.S. Pat. No. 4,686,191, U.S. Pat. No. 4,939,094, U.S. Pat. No. 5,160,735).

Any promoter which can express in a host cell such as *Escherichia coli* can be used. For example, it is a promoter from *Escherichia coli* or a phage such as trp promoter (Ptrp), lac promoter (Plac), PL promoter, PR promoter or PSE promoter, SPO1 promoter, SPO2 promoter or penP promoter. And a promoter artificially modified such as a promoter which two Ptrps is connected in series (Ptrp×2), tac promoter, lacT7 promoter or letI promoter can be used.

Preferred is a plasmid that the distance between Shine-Dalgarno sequence which is a ribosome binding sequence and an initiation codon is regulated to an appropriate distance, for example, 6 to 18 bases. A transcription termination sequence is not always needed for an expression of KIAA1036 polynucleotide but preferred is that a transcription termination sequence is positioned at the right downstream of a structural gene.

A host cell is, for example, a prokaryote of *Escherichia* genus, *Serratia* genus, *Bacillus* genus, *Brevibacterium* genus, *Corynebacterium* genus, *Microbacterium* genus or *Pseudomonas* genus, for example, XL1-Blue strain, XL2-Blue strain, DH1 strain, MC1000 strain, KY3276 strain, W1485 strain, JM109 strain, HB101 strain, No. 49 strain, W3110 strain, NY49 strain, BL21 (DE3) strain, BL21 (DE3) pLysS strain, HMS174 (DE3) strain or HMS174 (DE3) pLysS strain of *E. coli* as *Escherichia* genus, *S. ficaria* strain, *S. fonticola* strain, *S. liquefaciens* strain or *S. marcescens* strain as *Serratia* genus, *B. subtilis* strain or *B. amyloliquefaciens* strain as *Bacillus* genus, *B. ammoniagenes* strain, *B. Immariophilum* (ATCC:14068) strain or *B. saccharolyticum* (ATCC:14066) strain as *Brevibacterium* genus, *C. glutamicum* (ATCC:13032) strain, *C. glutamicum* (ATCC: 14067) strain, *C. glutamicum* (ATCC: 13869) strain or *C. acetoacidophilum* (ATCC: 13870) strain as *Corynebacterium* genus, *M. ammoniaphilum* (ATCC: 15354) strain as *Microbacterium* genus or *S. mephitica* strain as *Pseudomonas* genus.

Any method to introduce DNA to the above host cell can be used as an introduction method of a recombinant vector, for example, an electroporation (Nucleic Acids Research, 16, 6127 (1988).), calcium phosphate method (Proceedings of the National Academy of Sciences USA, 69, 2110 (1972).), a protoplast method (JP 1987-2483942) or the method described in Gene, 17, 107 (1982). or Molecular & General Genetics, 168, 111 (1979).

(ii) The Case that Yeast is Used as a Host.

When yeast is used as a host, an expression vector is, for example, YEp13 (ATCC:37115), YEp24 (ATCC:37051), YCp50 (ATCC:37419), pHS19 or pHS15.

Any promoter which express in yeast can be used as a promoter, for example, ADH1 (alcohol dehydrogenase) promoter, PHO5 (acid phosphatase) promoter, PGK1 (phosphoglycerate kinase) promoter, GAPDH (glyceraldehyde3-phosphate dehydrogenase) promoter, GAL1 (galactose kinase) promoter, GAL10 (UDP galactose4-epimerase) promoter, MF□1 (□pheromone) promoter or CUP1 (metallothionein) promoter.

A host is, for example, *S. cerevisiae* species of *Saccharomyces* genus, *S. pombe* species of *Schizosaccharomyces* genus, *K. lactis* species of *Kluyveromyces* genus, *T. pullulans* species of *Trichosporon* genus, *S. alluvius* species of *Schwanniomyces* genus or *P. pastoris* species of *Pichia* genus.

Any method to introduce DNA into a host can be used as a introduction method of a recombinant vector, for example, an electroporation (Methods in Enzymology, 194, 182 (1990).), a spheroplast method (Proceedings of the National Academy of Sciences USA, 84, 1929 (1978).) or a lithium acetate method (Journal of Bacteriology, 153, 163 (1983). or Proceedings of the National Academy of Sciences USA, 75, 1929 (1978).).

(iii) The Case that an Animal Cell is Used as a Host.

When an animal cell is used as a host, an expression vector is, for example, pcDNA1/Amp, pcDNA1, pCDM8, pREP4 (Invitrogen), pAGE107 (Cytotechnology, 3, 133 (1990).), pAGE103 (The Journal of Biochemistry, 101, 1307 (1987).), pAMo, pAMoA (pAMoPRSA) (The Journal of Biological Chemistry, 268, 22782-22787 (1993).) or pAS3-3 (JP1990-22705).

Any promoter that can express in a host can be used as a promoter, for example, a promoter of IE (Immediate-early) gene of human cytomegalovirus (hCMV), an early promoter of SV40, Long Terminal Repeat Promoter of Moloney Murine Leukemia Virus, a promoter of retrovirus, HSP promoter, SR□ promoter or a promoter of metallothionein. An enhancer of IE gene of human CMV can be used with a promoter.

An animal cell as a host is, for example, HEK293 (a human fetal nephrocyte, ATCC:CRL-1573), Namalwa (Burkitt lymphoma, ATCC:CRL-1432), HeLa (a cell of carcinoma of uterine cervix, ATCC:CCL-2), HBT5637 (a leukemia cell, JP1987-299), BALL-1 (a leukemia cell) or HCT-15 (a large bowel cancer cell) of an established cell from a human, Sp2/0-Ag14 (a mouse myeloma cell, ATCC:CRL-1581) or NSO (a mouse myeloma cell) of an established cell from a mouse, COS-1 (African green monkey nephrocyte (SV40 transformed cell), ATCC:CRL-1650) or COS-7 (African green monkey nephrocyte (SV40 transformed cell), ATCC:CRL-1651) of an established cell from a monkey, CHO-K1 (Chinese hamster ovary cell, ATCC:CCL-61) or BHK-21 (C-13) (Sicilian hamster kidney cell, ATCC:CCL-10) of an established cell from a hamster, PC12 (an adrenal pheochromocytoma, ATCC:CRL-1721) or YB2/0 (a rat myeloma cell, ATCC:CRL-1662) of an established cell from a rat.

Any method to introduce DNA into a host can be used as an introduction method of a recombinant vector, for example, an electroporation (Cytotechnology, 3, 133, (1990).), a calcium phosphate method (JP1990-22705) or a lipofection method (Proceedings of the National Academy of Sciences, USA, 84, 7413 (1987). or Virology, 52, 456 (1973).).

(iv) The Case that a Plant Cell is Used as a Host.

When a plant cell or a plant is used as a host, a polypeptide can be produced as well as a well-known method (The Tissue Culture, 20 (1994), The Tissue Culture, 21 (1995). or Trends in Biotechnology, 15, 45 (1997).). An expression vector is, for example, Ti plasmid or Tobacco mosaic virus vector. Any promoter that can express in a plant cell can be used as a promoter for a gene expression, for example, 35S promoter of Cauliflower mosaic virus (CaMV) or Rice actin 1 promoter. And expression productivity of a gene can be enhanced by inserting intron 1 of an alcohol dehydrogenase gene of maize between a promoter and an expressed.

A host is, for example, a plant cell such as potato, tobacco, maize, rice, rape, soybean, tomato, carrot, wheat, barley, rye, alfalfa or flax.

Any method to introduce DNA into a host can be used as a introduction method of a recombinant vector, for example, a method with *Agrobacterium* (JP1983-140885, JP1984-70080 or WO94/00977), an electroporation (JP1984-251887) or a particle gun (gene gun) method (JP2606856, JP2517813).

(v) The Case that an Insect Cell is Used as a Host.

When an insect cell is used as a host, a transfer vector is, for example, pVL1392, pVL1393 or pBlueBacIII (Invitrogen) and a virus for infection is, for example, a Vaculovirus which infects insects of *Mamestra* brassicoe family; *Autographa california* nuclear polyhedrosis virus (AcMNPV) Bac-N-Blue DNA. A transformation method of an insect cell is, for example, a method described in Baculovirus Expression Vector: A Laboratory Manual (1992) (W.H. Freeman and Company), Molecular Cloning: A Laboratory Manual, Second Edition (1989) (Cold Spring Harbor Laboratory Press), Current Protocols in Molecular Biology (1994) (Wiley-Inter-Science) or Biotechnology, 6, 47 (1988).

A transfer vector including a target gene and baculovirus DNA for infection to an insect cell are added into a culture and a virus expressing a target gene produced by recombinant infects an insect cell to be expressed a polypeptide.

An insect cell as a host is, for example, an established cell from *Spodoptera frugiperda* (*Mamestra* brassicoe) or an established cell from *Trichoplusia ni*. For example, a cell from *S. frugiperda* includes Sf9 (ATCC: CRL-1711, an ovary cell) or Sf21 (an ovary cell) and a cell strain from *T. ni* is, for example, High Five or BTI-TN-5B1-4 (an egg cell, Invitrogen).

Any method to introduce DNA into a host can be used as an introduction method of a recombinant vector, for example, a calcium phosphate method (JP1990-22705) or a lipofection method (Proceedings of the National Academy of Sciences USA, 84, 7413 (1987).). And an electroporation (Cytotechnology, 3, 133 (1990).) can be used as well as an animal cell.

(vi) A Culture Method

When a transformant having a recombinant vector with an inserted DNA encoding KIAA1036 polypeptide of the present invention is a cell such as *Escherichia coli*, yeast, an animal cell or a plant cell, a cultivation by a usual culture method suited to all kinds of hosts is held. And the polypeptides are produced, accumulated and collected from transformants or a culture solution to produce the polypeptide. When transformants are animals or plants, they are cultured by a usual growth method suited to all kinds of hosts. And the polypeptides are produced, accumulated and collected from animals or plants to produce the polypeptide.

When a host is an animal, for example, a nonhuman transgenic animal having polynucleotides of the present invention is cultured. And KIAA1036 polypeptides encoded by the recombinant DNA are produced and accumulated in the animal and they are collected from an animal to produce KIAA1036 polypeptides. A production/accumulation place in an animal is, for example, milk, sputum or egg of the animal.

When a host is a plant, for example, a transgenic plant having KIAA1036 polynucleotides of the present invention is cultured. And KIAA1036 polypeptides encoded by the recombinant DNA are produced or accumulated in a plant and collected from a plant to produce KIAAl036 polypeptides.

When a host is a prokaryote such as *Escherichia coli* or a eucaryote such as yeast, for example, transformants having polynucleotides of the present invention are cultured in a medium. And KIAA1036 polypeptides encoded by the recombinant DNA are produced or accumulated in a culture solution and collected from the culture to produce polypeptides of the present invention.

The method that transformants of KIAA1036 of the present invention are cultured in a medium is accomplished by a usual method for cultivation.

When a host is prokaryote such as *Escherichia coli* or a eucaryote, a natural medium or a synthetic medium can be used as a medium that obtained transformants are cultured if it has a carbon source, a nitrogen source and mineral that a host can assimilate and it is a medium that cultivation of transformants is held efficiently. For example, YT medium including bactotryptone, yeast extract and sodium chloride is preferable as a medium when transformants that hosts are *Escherichia coli* are cultured.

Any carbon source that each microorganism can assimilate can be used, for example, glucose, fructose, sucrose, syrup including them, carbohydrate such as starch or starch hydrolysate, an organic acid such as acetic acid or propionic acid or alcohol such as ethanol or propanol.

A nitrogen source is, for example, all kinds of inorganic acids such ammonia, ammonium chloride, ammonium sulfate, ammonium acetate, ammonium phosphate, ammonium salts of organic acids, other nitrogenous substances, peptone, meat extract, yeast extract, Corn Steep Liquor, casein hydrolysate, soybean cake, soybean cake hydrolysate, all kinds of fermentative bacteria or the digest.

A mineral is, for example, potassium phosphate monobasic, potassium phosphate dibasic, magnesium phosphate, magnesium sulfate, sodium chloride, ferrous sulfate, manganese sulfate, copper sulfate or calcium carbonate. Cultivation is held under an aerobic condition such as a shaking culture or a submerged culture.

An incubation temperature is preferably 15 to 40° C. and a culture time is usually 5 hours to 7 days. During cultivation, pH is kept from 3.0 to 9.0. Adjustment of pH is held with mineral or organic acid, alkali solution, urea, calcium carbonate or ammonia. And an antibiotic such as ampicillin or tetracycline can be optionally added into a medium during cultivation.

When microorganisms transforming with an expression vector with an inductive promoter are cultured, inducers can be optionally added into a medium. For example, when transformants transforming with an expression vector with lac promoter are cultured, isopropyl β-D-thiogalactopyranoside can be added into a medium. When transformants transforming with an expression vector with trp promoter are cultured, indoleacrylic acid can be added into a medium. Cells and organs of plants introduced genes can do a mass culture with jar fermenter. A culture medium is, for example, popularly used Murashige & Skoog (MS) medium, White medium, or a medium that plant hormones such as oxine or cytokinin are added into these mediums.

When transformants for production of KIAA1036 polypeptide are animal cells, a medium that cells are cultured is popularly used RPMI1640 medium (The Journal of the American Medical Association, 199, 519 (1967).), MEM medium (Science, 130, 432 (1959).), D-MEM medium (Virology, 8, 396 (1959).), 199 medium (Proceedings of the Society for the Biological Medicine, 73, 1 (1950).) or a medium that fetal calf serum (FCS) is added into these mediums.

Cultivation held usually in pH 6 to 8, at 25 to 40° C., in the presence of 5% $CO_2$ for 1 to 7 days. And an antibiotic such as kanamycin, penicillin or streptomycin can be optionally added into a medium during cultivation.

When transformants are insect cells, a culture medium is popularly used TNM-FH medium (Pharmingen), Sf-900II SFM medium (Invitrogen), ExCell400, ExCell405 (JRH Biosciences Inc.) or Grace's Insect Medium (Nature, 195, 788 (1962).).

(vii) The Method of Production

Transformants are cultured and KIAA1036 polypeptides are isolated and purified from a culture to produce KIAA1036 polypeptides. A method of isolation/purification of KIAA1036 polypeptides can be usual method widely known in this field, for example, a method of isolation/purification of an enzyme or a method of purification of transglucosylase by Sandler (Methods in Enzymology, 83, 458).

When KIAA1036 polypeptides are produced and accumulated as dissolved polypeptides, a culture solution that transformants are cultured as mentioned above is separated to cells or fungus body and a medium, for example, by a centrifugal separation. When KIAA1036 polypeptides exist in host cells, after cells or fungus bodies extracted are washed with an appropriate buffer such as STE solution and broken into pieces by ultrasonic waves, French press, Manton Gaulin homogenizer or Dynomill, KIAA polypeptides can be obtained as an acellular solution by a centrifugal separation or a filtration.

The suitable quantity of surfactant can be included in a buffer for separation/purification of KIAA1036 polypeptide.

For example, sodium lauryl sulfate (SDS) or Sodium N-Dodecanoylsarcosinate (sarcosyl) can be used.

A method of separation/purification of target proteins included in an obtained crude material can be accomplished with the combination of all kinds of well-known methods of separation/purification. The well-known method is, for example, a solvent extraction method, a salting-out method with ammonium sulfate, a dialysis, an sedimentation with an organic solvent, an ultrafiltration method, a gel filtration, all kinds of chromatography such as a diethylaminoethyl (DEAE)-sepharose chromatography, an anion chromatography or an ion exchange chromatography using lysine such as DIAION HPA-75 (Mitsubishi Chemical Corporation), a cation chromatography using lysine such as S-Sepharose FF (Pharmacia), a hydrophobic chromatography or an affinity chromatography such as butylsepharose or all kinds of electrophoresis such as a SDS-polyacrylamide gel electrophoresis or an electro-focussing electrophoresis. An affinity chromatography can be accomplished by using antibodies against KIAA1036 polypeptide.

When KIAA1036 polypeptides are produced and accumulated as insoluble polypeptides, cells or fungus bodies are separated as mentioned above and broken into pieces by an appropriate method. Then a division including the polypeptides is collected. A collected sample is solubilized with a solubilizer like a surfactant such as sodium lauryl sulfate (SDS) or Sodium N-Dodecanoylsarcosinate (sarcosyl). After the solubilized solution is diluted or dialyzed to the concentration that a solubilizer is not or almost not included and the polypeptide is constructed to a normal stereo structure, a purification sample can be obtained by a method of separation/purification as mentioned above.

And KIAA1036 polypeptides can be produced as fusion proteins with the other proteins and purified by an affinity chromatography with substances having affinity with the fusion proteins (Yamakawa Akio, "Experimental Medicine", 13, 469-474 (1995).). An addition protein used as a fusion protein is, for example, protein A or FLAG (Proceedings of the National Academy of Sciences USA, 86, 8227 (1989), Genes Development, 4, 1288 (1990), JP1993-336963 or JP1994-823021). When protein A are used, fusion proteins with KIAA1036 polypeptides and protein A can be produced and purified by an affinity chromatography with immunoglobulin G. When FLAG peptides are used, fusion proteins with KIAA1036 polypeptides and FLAG can be produced and purified by an affinity chromatography with anti-FLAG antibodies.

KIAA1036 polypeptides can be produced as well as a well-known method with in vitro transcription/translation system (Journal of Biomolecular NMR, 6, 129-134 (1995), Science, 242, 1162-1164 (1988). or The Journal of Biochemistry, 110, 166-168 (1991).).

KIAA1036 polypeptides can be chemosynthesized on the basis of the amino acid sequence by a chemical synthesis method such as Fmo method (Fluorenylmethyl oxycarbonyl method) or tBoc method (t-butyl oxycarbonyl method), or by a peptide synthetic equipment on the market such as, for example, APEX396 (Advanced Chemtech), 433A (Applied Biosystems), PS3 (Protein Technologies), 9050 (Perseptive) or PSSM-8 (Shimazu corporation).

A structural analysis of KIAA1036 polypeptide can be accomplished by a usual method in the field of protein chemistry, for example, a method described in "A protein structural analysis for gene cloning" (Hisashi Hirano, TOKYO KAGAKU DOZIN Co., LTD., 1993). The chordin activity of a polypeptide of the present invention can be measured as well as a well-known assay (The Journal of Biological Chemistry, 258, 9893-9898 (1983), The Journal of Biological Chemistry, 262, 15649-15658 (1987), The Journal of Biological Chemistry, 273, 58-65 (1998), The Journal of Biological Chemistry, 273, 433-440 (1998), The Journal of Biological Chemistry, 273, 12770-12778 (1998), Archives of Biochemistry and Biophysics, 270, 630-646 (1989), Archives of Biochemistry and Biophysics, 274, 14-25 (1989). or JP1994-181759).

(3) A Method of Production of a Variant Polypeptide Mutation

A deletion, a substitution or an addition of an amino acid of KIAA1036 polypeptide is accomplished by a widely known technique, a site-specific potentially mutagenic method. A deletion, a substitution or an addition of 1 or few amino acid(s) can be prepared as well as the method described in Molecular Cloning: A Laboratory Manual, Second Edition (1989) (Cold Spring Harbor Laboratory Press.), Current Protocols in Molecular Biology (1994) (Wiley-InterScience), Nucleic Acids Research, 10, 6487 (1982), Proceedings of the National Academy of Sciences USA, 79, 6409 (1982), Gene, 34, 315 (1985), Nucleic Acids Research, 13, 4431 (1985), Proceedings of the National Academy of Sciences USA, 82, 488 (1985), Proceedings of the National Academy of Sciences USA, 81, 5662 (1984), Science, 224, 1431 (1984), WO85/00817 or Nature, 316, 601 (1985).

(4) A Production of an Antibody Against KIAA1036 Polypeptide (i) A Production of a Polyclonal Antibody Antibodies can be produced by giving all length of KIAA1036 polypeptides, a part of the peptides or polypeptides including a part of the peptides as antigens to a mammal. The peptide itself and a carrier, for example, a carrier combined with cattle serum albumin (BSA), keyhole limpet hemocyanin (KLH) or bovine thyroglobulin (BTG) can be used as an antigen. To enhance immune reactions with antigens, for example, a complete Freund adjuvants (CFA) and an incomplete Freund adjuvants (IFA) can be given. A mouse, a rat, a rabbit, a goat or a hamster can be used as a mammal to immunize.

Polyclonal antibodies can be produced, for example, as well as the method by Lane et al. (Antibodies: A Laboratory Manual, Second Edition (1989) (Cold Spring Harber Laboratory Press)).

After the first immunization, a mammal is immunized by an appropriate antigen 3 to 10 times at 1- to 2-week intervals. And then a serum from the mammal is extracted and purified to produce the antibodies.

The antigens are given 3 to 10 times at 1- to 2-week intervals. A preferable dosage of the antigens is 50 to 100 μg at one time per an animal. When peptides are used, peptides covalently bonded to appropriate carriers are preferably used as antigens. Peptides as antigens can be synthesized by a method of genetic engineering or a peptide synthesizer. Three to seven days after immunization, the blood from venous plexus of eyegrounds is collected and the responsiveness of the serum against the antigens can be measured by an enzyme-liked-immunosorbent assay (Enzyme-liked-immunosorbent assay (ELISA): Igaku-Shoin Ltd. (1976), Antibodies: A Laboratory Manual, Second Edition (1989) (Cold Spring Harbor Laboratory Press).

Blood is collected from a mammal immunized and an antibody titer is measured. Blood is collected when the immunized animal shows a sufficient antibody titer, and then polyclonal antibodies can be prepared from the serum. Separation and purification of polyclonal antibodies can be accomplished by an individual or a combination of all kinds of chromatography such as a centrifugal separation, salting-out with ammonium sulfate, precipitation with caprylic acid (Antibodies: A Laboratory Manual, Second Edition (1989) (Cold Spring Harbor Laboratory Press), DEAE-sepharose column, anion exchange column, protein A column or G-column or a gel filter column.

(ii) A Production of a Monoclonal Antibody (a) A Preparation of an Antibody Producing Cell After a sufficient antibody titer in (i) is obtained, spleen or lymph node is extracted from the mammal. And then a monoclonal antibody producing hybridoma can be obtained by fusing an antibody-producing cell from the spleen or lymph node with a myeloma cell. As for the myeloma cell, cell strains established from a mouse or a rat can be used. Cell fusion can be done according to an already known method, for example, a method by Kohler and Milstein (Nature, 256, 495-497 (1975).).

KIAA1036 polypeptides, a part of the peptides or polypeptides including the part of the peptides are immunized to a rat. Three to seven days after a rat showed a sufficient antibody titer, the rat is immunized with the antigen for the last time, and its spleen is extracted as antibody producing cells. The spleen is cut to pieces in MEM medium (Nissui Pharmaceutical Co. Ltd.) and untied with tweezers. And then a precipitant is obtained after a centrifugation at 1,200 rpm for 5 minutes. Splenocytes is separated by treating the precipitant with Tris-ammonium chloride buffer (pH 7.65) for 1 to 2 minutes to remove red blood cells. The splenocytes are washed with MEM medium 3 times and are used as antibody producing cells.

(b) A Preparation of a Myeloma Cell

An established cell line from mouse or rat is used as a myeloma cell. For example, it is a myeloma cell of 8-azaguanine resistance mouse (from BALB/c), P3-X63Ag8-U1 strain (described below as P3-U1) (Current Topics Microbiological Immunology, 81, 1 (1978). or European Journal of Immunology, 6, 511 (1976).), SP2/0-Ag14 strain (described below as SP-2) (Nature, 276, 269 (1978).), P3-X63-Ag8653 strain (described below as 653) (Journal of Immunology, 123, 1548 (1979).) or P3-X63-Ag8 (described below as X63) (Nature, 256, 495 (1975).). These cell strains are subcultured in a 8-azaguanine medium (a normal medium including 15 μg/ml 8-azaguanine (RPMI1640 medium including 1.5 mM glutamine, $5 \times 10^{-5}$ M 2-mercaptoethanol, 10 μg/ml gentamycin and 10% FCS made by CSL)) and cultured in a normal medium for 3 to 4 days before cell fusion. $2 \times 10^7$ or more cells are prepared for cell fusion.

(c) A Production of Hybridoma

Antibody producing cells prepared in (a) and myeloma cells prepared in (b) are washed with MEM medium or PBS (per IL; 1.83 g sodium phosphate dibasic, 0.21 g monobasic potassium phosphate, 7.65 g NaCl, pH 7.2) and mixed as the number of antibody producing cells is 5 to 10 times larger than that of the myeloma cells. After a centrifugal separation at 1,200 rpm for 5 minutes, a precipitant is obtained. The precipitated cells are well untied and 0.2 to 1 ml of polyethylene glycol solution (2 g polyethylene glycol-1000 (PEG-1000), 2 ml MEM medium, 0.7 ml dimethyl sulfoxide (DMSO)) per 108 antibody producing cells is added to the cells with stirring at 37° C. And then 1 to 2 ml of MEM medium is added for several times every 1 to 2 minutes. The solution is prepared with MEM medium to 50 ml in total. After a centrifugal separation at 900 rpm for 5 minutes, a precipitant is obtained. 100 ml of HAT medium (normal medium including $10^{-4}$ M hypoxanthine, $1.5 \times 10^{-5}$ M thymidine and $4 \times 10^{-7}$ M aminopterin) is added to a precipitant and the precipitant is untied slowly and suspended.

The suspension is poured into the 96-well culture plate at 100 μl per well and cultured at 37° C. in the presence of 5% $CO_2$ for 7 to 14 days. By the method described in "enzyme immunoassay" (Antibodies: A Laboratory Manual, Second Edition (1989) (Cold Spring Harbor Laboratory Press)), hybridomas producing antibodies specifically reacting with KIAA1036 polypeptides are selected.

(5) An Immunoassay of KIAA 1036 Polypeptide

The method to measure polypeptides or a part of the peptides by using antibodies that recognize the polypeptides or a part of the peptides and are directly or indirectly bonded to enzymes, fluorescent substances, radioisotopes or latexes can be used as an immunoassay of KIAA 1036 polypeptides. The assay is, for example, ELISA or a chemiluminescence method detecting enzyme activities such as horseradish peroxidase or alkaline phosphatase, FITC method detecting fluorescent tags such as luminol or GFP (Green Fluorescence Protein), RIA method detecting radioisotope tags such as $^{125}\square$ or a latex agglutination method detecting binding with latex.

And the assay is, for example, Western blotting or an immune structure dyeing method.

Furthermore, KIAA1036 polypeptides or a part of peptides can be quantitated by the assay.

Antibodies for an immunoassay can be immobilized to a solid phase carrier and the trapped polypeptides can be detected by using secondary antibodies with a reporter group or using reagents. A competitive method that KIAA1036 polypeptides are labeled with a reporter group, reacted with antibodies and a sample and bonded with immobilized antibodies can be used to detect. The level of inhibition the binding between the labeled polypeptides and antibodies by KIAA1036 polypeptides of a sample is shown by reactivity with immobilized antibodies of a sample and the concentration of KIAA1036 polypeptides in a sample can be calculated. Any substance, to which antibodies can attach and which is widely known to a parson having ordinary skill in the art, can be used as a solid phase carrier. The substance includes, for example, a microtitre plate, a membrane such as a nitrocellulose membrane, bead, disk, glass, glass fiber, plastic material such as latex, polystyrene or polyvinyl chloride. Magnetic particles or fiber optical sensors (U.S. Pat. No. 5,359,681) can be used. A well-known method used in this field can be used as a method which antibodies are immobilized to a carrier. In this description, "solid phase" means immobilization by a physical method such as adsorption or a chemical binding by a covalent bond between an antibody and a functional group on a carrier. An antibody and a functional group on a carrier can be bonded directly or through a cross-linking agent.

Immobilization by a physical method can be accomplished by appropriately diluted antibodies contacted with a carrier, preferably, a microtiter plate or a membrane in an appropriate buffer for an appropriate time. The contact time varies depending on the temperature, but it is typically between about 1 hour and 1 day. About 10 ng to 1 μg, preferably, about 100 to 200 ng of antibodies is added and immobilized on each well of a microtiter plate made of plastic such as polystyrene or polyvinyl chloride.

Immobilization by a chemical method can be accomplished by a reaction of a carrier and functional groups of antibodies, for example, a reaction of a carrier and a two-functional reagent that reacts with both hydroxyl groups and amino groups and a carrier. For example, antibodies can be immobilized to a carrier having an appropriate polymer coat with a covalent bond by using benzoquinone or a condensation between aldehyde groups on a carrier and an amine or an active hydrogen on a combination partner. The method can be accomplished by using for example, Pierce immunotechnology Catalog and Handbook (1991) A12 to A13 as a reference.

A carrier-immobilized antibody is treated to inhibit physical adsorption of other polypeptides by a well-known method for a parson having ordinary skill in the art with an appropriate blocking reagent, for example, cattle serum albumin or Tween 20 (Sigma-Aldrich).

A carrier-immobilized antibody is reacted with a sample and polypeptides of the present invention and antibodies are combined. A sample can be appropriately diluted with an appropriate diluent, for example, phosphate buffered saline solution (PBS). A reaction time of a sample and antibodies should be enough to detect the presence of polypeptides of the present invention in a sample obtained from an individual having a cancer, preferably, a time to achieve at least 95% of binding level compared to the level at which bound and not-bound polypeptides are equilibrated. A time to reach to equilibrium can be easily decided by measuring the binding level by the time. Substances other than bound polypeptides can be removed by washing a solid carrier with an appropriate buffer, for example, PBS (including 0.1% Tween 20). Labeled secondary antibodies are reacted with a solid carrier. The labels are preferably enzymes such as horseradish peroxidase, ground substances, supplemental elements, inhibitors, pigments, radioisotopes, coloring substances or fluorescent substances. The binding between antibodies and labels can be accomplished by a well-known method for a parson having ordinary skill in the art. The secondary antibodies are reacted for a sufficient time to bind to complexes, which include immobilized antibodies and polypeptides of the present invention. An appropriate time can be easily decided by measuring binding level by the time. The non-binding secondary antibodies can be removed by washing a solid carrier with an appropriate buffer, for example, PBS (including 0.1% Tween 20). The method of detection of labels of the secondary antibodies is different by a kind of labels. When radioisotopes are used as labels, detection by a scintillation counter or an autoradiography can be used. When pigments, coloring substances or fluorescent substances are used as labels, detection by a spectrophotometer can be used. When enzymes are used as labels, ground substances against the enzymes are added and reacted for a fixed time and the products are detected by a spectrophotometer. Labels and secondary antibodies can bind directly or indirectly by an avidin-biotin method. When they bind indirectly, one part of the avidin-biotin is bound to a secondary antibody and another is bound to a label. KIAA1036 polypeptides can be detected by a flow through test or a strip test. In a flow through test, a sample is added to a nitrocellulose membrane on which antibodies are immobilized, and when a sample passes through the membrane, polypeptides bind to the immobilized antibodies to form immune complexes. And when a solution including labeled secondary antibodies pass through the membrane, it binds to the immune complexes. In a strip test, once a sample is added, the sample pass through a region including labeled antibodies, and polypeptides bind to labeled antibodies to form immune complexes. When a sample pass through a region including a solid phase antibodies, polypeptides bind to the immune complexes. The quantity of secondary antibodies detected in the region with immobilized antibodies shows the presence or absence of cancer. Labels in the detection part can be visualized for confirmation. If it can not be confirmed, it shows a negative result. A quantity of antibodies immobilized to a membrane is preferably about 25 ng to 1 μg and more preferably about 50 ng to 1 μg.

(6) An Assay of mRNA

Using oligonucleotides prepared from KIAA1036 polynucleotides, mRNAs are quantitated by Northern hybridization or RT-PCR, and then expression level of a gene encoding KIAA1036 polypeptide can be quantitated.

When mRNAs are quantitated with normal or disease model animals, for example, mice, rats, rabbits, sheep, pigs, cattle, cats, dogs or monkeys, an agent such as an anticancer agent is optionally given. After a fixed time, organs or tissues such as blood, brain, stomach or kidney is isolated and cells are prepared. mRNAs can be extracted from obtained cells by a widely known and usual method in this field and quantitated/analyzed by RT-PCR or Northern blot hybridization.

When mRNAs from transformants, which express KIAA1036 polypeptides or a part of the peptides, are quantitated, mRNAs can be extracted from the transformants by a widely known and usual method in this field and quantitated/analyzed by RT-PCR or Northern blot hybridization.

(7) Identification of a Structure of the Gene

Recently, a lot of sequences of human genome whose functions are unknown are registered on databases. Therefore, by comparing KIAA1036 polynucleotide sequence and a sequence of human genome registered on databases, human gene encoding KIAA1036 polypeptide can be identified and a structure of the gene can be clarified. If a genomic sequence, which coincides with cDNA sequence, is registered, a promoter region and a structure of exon and intron of the gene encoding a polypeptide of the present invention can be screened by comparing cDNA sequence and a sequence of the gene. By using KIAA1036 polynucleotide as a probe and a widely known and usual method in this field (Division of Oncology, Institute of Medical Science, Univ. of Tokyo, New Protocol for Molecular and Cellular Biology, Shujunsha (1993).), a promoter region of the gene can be obtained. Promoter regions are all of the promoter regions concerned with transcription of a gene encoding KIAA1036 polypeptide in mammal cells.

(8) A Method of Detection of Disease

KIAA1036 polypeptides can be used for diagnosis of diseases relating to neovaucularization, for example, vascular disease, inflammatory disease, entoptic neovascular disease, reproductive system disease, central nervous system disease or cancer because the expression is increased in angiogenesis models. Furthermore, because the expression of the polypeptides is increased in ovarian cancer and large bowel cancer tissue, it can be used for diagnosis of these cancers. Polypeptides of the present invention or polynucleotides such as mRNAs are specifically detected from biological samples, for example, cancer or normal tissue specimen, dissected tissue, blood, lymph node, serum, urine or other tissues obtained from a patient and their homogenates or extracts. Then presence or absence of cancer in a patient can be decided by comparing the expression level in a patient with a level in a normal person or a normal tissue.

The method of detection of disease includes, for example, an immunoassay or a molecular-biological method of detection of the polypeptides.

An immunoassay of the polypeptides includes, for example, sandwich ELISA. In this method, a pair of antibodies recognizing different epitopes of the polypeptide are used and one antibody is labeled directly or indirectly with an enzyme. Another method is a competitive RIA by using the polypeptides labeled with radioisotopes such as $^{125}$I and antibodies recognized them.

A molecular-biological method of detection includes, for example, in situ hybridization or PCR. PCR can be used to amplify cDNA prepared from mRNA isolated from a biological sample from a patient. A primer for PCR can be chemically synthesized on the basis of DNA sequence of SEQ ID NO: 1. Preferred is Primer1 which is an oligonucleotide sequence of SEQ ID NO: 4,5'-GTTCAGGACT-GTCTTTCAGC-3', or Primer2 which is an oligonucleotide sequence of SEQ ID NO: 5,5'-GTCAATACTGATGGACT-TGC-3'. cDNA amplified by PCR can be separated by gel electrophoresis and then turned visible by the method widely known to a parson having ordinary skill in the art. Usually, samples are appropriately prepared from a pair of tissues, which are a cancer tissue and a normal tissue from the same individual or different individuals and subjected to PCR. An amplification reaction by PCR is preferably held with a serial two orders dilution of template cDNAs. In some dilution points, more than two-fold increase in expression of a cancer sample compared to a normal sample is considered as a positive result.

The presence or absence of cancer is judged by measuring markers of the present invention detected in a normal sample and a patient sample and comparing. Generally, a mean value of markers from a healthy person without cancer is considered as a cut-off value and the cut-off value is compared to detected value of markers from a patient sample. Generally, when the detected value is over three times of the standard deviation plus a cut-off value, the sample is considered as a positive about cancer. And a cut-off value is decided by Receiver Oparator Curve described in Sackett et al., Clinical Epidemiology: A Basic Science for Clinical Medicene 106-107, (1985) (Little Brown and Co).

(9) A Diagnostic Kit

KIAA1036 polynucleotides can be used for a diagnosis of neovascularization related disease, for example, vascular disease, inflammatory disease, entoptic neovascular disease, reproductive system disease, central nervous system disease or cancer such as ovarian cancer or large bowel by Northern hybridization or PCR. And a diagnosis of neovascularization related disease, for example, vascular disease, inflammatory disease, entoptic neovascular disease, reproductive system disease, central nervous system disease or cancer such as ovarian cancer or large bowel can be held by an immunologic method with antibodies against KIAA1036 polypeptides. Therefore, in the case of a diagnosis with polynucleotides, labeled KIAA1036 polynucleotides are contained in a kit. And in the case of a diagnosis with antibodies, KIAA1036 polypeptides are contained as standard antigens in addition to antibodies against KIAA1036 polypeptides. In a kit, a standard curve can be contained.

(10) The Method to Inhibit mRNA Translation

Giving KIAA1036 polynucleotides can inhibit the production of KIAA1036 polypeptides. Namely, by using KIAA1036 polynucleotides, transcription of DNA encoding KIAA1036 polypeptide and translation of mRNA encoding the polypeptide can be inhibited.

(11) The Screening Method of Binding Substances

As a reagent for search or screening binding substances to markers of the present invention, KIAA1036 polypeptides are useful. Namely, the screening method of binding substances to markers of the present invention, which comprises contact between markers and subjects, is provided. Subjects include, for example, chemical substances synthesized naturally or chemically, proteins, tissue extracts of a mammal such as human, mouse, rat, pig, cattle, sheep or monkey or cell culture. These subjects are added to markers of the present invention and the mixture is separated with measuring DNA synthesis activity of vascular endothelial cells. Finally, single ligands can be obtained.

For example, the screening method of binding substances of the present invention includes a method by using KIAA1036 polypeptides or the partial peptides, by constructing an expression system of recombinant polypeptides and using a binding assay with the expression system, by binding to KIAA1036 polypeptides and measuring cell stimulatory activity, for example, activity to promote or inhibit DNA synthesis by bringing BrdU (bromodeoxyuridine) or cell migrating activity or by measuring visually network formation of vascular endothelial cells with microscope.

At first, any polypeptide comprising polypeptide B can be used as polypeptides for the screening method of the binding substances but polypeptides expressed massively with animal cells is preferable. To produce polypeptide B, the above mentioned expression method is used, but the method is preferable when it includes expressing DNA encoding the polypeptide in mammal cells or insect cells. Generally cDNA is used as a fragment which encodes a protein to be expressed, but it should not be always cDNAs but fragment from genomic DNA or synthetic DNA can be used. To introduce DNA fragments encoding KIAA1036 polypeptides into host animal cells and effectively express them, it is preferable that the DNA fragments are inserted downstream of a polyhedrin promoter of nuclear polyhedrosis virus(NPV) of baculovirus which use insects as a host, a promoter from SV40, a promoter of retrovirus, a metallothionein promoter, a human heat-shock promoter, a cytomegalovirus promoter or a SR □ promoter. The examination of quantity and quality of expressed polypeptides can be done by a well-known method. For example, it is the method described in The Journal of Biological Chemistry, 267, 19555 to 19559 (1992).

Therefore, in a screening method of binding substances of the present invention, polypeptides or the partial peptides purified by the well-known method, cells including the polypeptides or their supernatants can be used as a thing including KIAA1036 polypeptides or the partial peptides. In a screening method of binding substances of the present invention, when cells including KIAA1036 polypeptides are used, that cells can be immobilized to agarose gel. The method of immobilization can be held by the well-known method. Cells including KIAA1036 polypeptides mean host cells with expressing KIAA1036 polypeptides. For example, *Escherichia coli, Bacillus subtilis*, yeast, insect cells and animal cells are used as the host cells.

For the screening of binding substances to KIAA1036 polypeptides, appropriate polypeptide fractions and labeled test substances are needed. As a polypeptide fraction, for example, a natural polypeptide fraction or a recombinant polypeptide fraction having the same activity as a natural one is preferable. The same activity means, for example, the same ligand binding activity or the same signal transduction activity. The labeled test substances are, for example, substances labeled with $^3$H, $^{125}$I, $^{14}$C or $^{35}$S.

For example, for a screening method of binding substances to KIAA1036 polypeptides, at first, a polypeptide sample is prepared by suspending cells including KIAA1036 polypeptides or a membrane fraction of the cells in a buffer which is suitable for a screening method. Any buffer, which does not inhibit combining a ligand and a polypeptide, for example, a phosphoric acid buffer that is pH4 to 10, preferably pH6 to 8 or a Tris-HCl buffer is used as a buffer. And to decrease non-specific binding, a surfactant, for example, CHAPS, Tween-80 (Kao-Atlas), digitonin or deoxycolate or all kinds of protein, for example, cattle serum albumin or gelatin can be added into the buffer. Furthermore, to repress degradation of receptors and ligands by protease, a protease inhibitor, for example, PMSF, leupeptin, E-64 (PEPTIDE INSTITUTE, INC.) or pepstatin can be added. Test substances are labeled with, for example, constant quantity, preferably 5000 cpm to 500000 cpm of $^3H$, $^{125}I$, $^{14}C$ or $^{35}S$ are coexistence in 0.01 to 10 ml of the polypeptide solution. To measure the quantity of non-specific binding (NSB), a reaction tube with excessive amount of unlabeled test substances is also prepared. The reaction is held at 0° C. to 50° C., preferably at 4° C. to 37° C., for 20 minutes to 24 hours, preferably for 30 minutes to 3 hours. After the reaction, the solution is filtered by glass fiber filter papers and washed with a suitable quantity of the same buffer. The radioactivity remaining on the glass fiber filter paper is measured by a liquid scintillation counter or a □-counter. Test substances that the count (B-NSB), the result obtained by subtracting quantity of non-specific binding (NSB) from all quantity of binding (B), is over 0 cpm can be selected as binding substances to markers of the present invention.

For the screening of binding substances to markers of the present invention, cell stimulatory activity through the polypeptides, for example, activity to promote or inhibit DNA synthesis by bringing BrdU (bromodeoxyuridine) or cell migrating activity can be measured by well-known method or a measuring kit on the market. And the activity can be measured by measuring visually network formation of vascular endothelial cells with microscope. For example, at first, cells including polypeptides are cultured on the multi-well plate. When the screening of binding substances is held, in advance, medium or buffer changes to fresh medium or appropriate buffer, which is non-toxic to cells and test substances are added. After incubation for a fixed time, cells are extracted or their supernatants are collected and the products are quantitated by the method for them. L

(12) A Kit for Screening of Binding Substances

A kit for screening of binding substances bonded to markers of the present invention is a kit comprising cells expressing polypeptide B or the polypeptides or their supernatant fraction including the polypeptides. The examples of a kit for screening of binding substances are the followings.

(i) A Reagent for Screening of Binding Substances

As a screening solution and washing solution, a solution that Hank's Balanced Salt Solution (Invitrogen) added 0.05% cattle serum albumin (SIGMA-Aldrich) is sterilized by filtration with 45 g/m filter, and it is kept at 4° C. or prepared just before use.

(a) COS-7 cells expressing polypeptides of the present invention are cultured on a 12-well plate with $5\times10^5$ cells/well and cultured at 37° C. for 2 days.

(b) A labeled subject

A solution containing commercially available subjects labeled with $^3H$, $^{125}I$, $^{14}C$ or $^{35}S$ is kept at 4° C. or 20° C., and diluted to 1 µM with assay buffer just before use. Subjects with the low solubility to water are dissolved in dimethyl formamide, DMSO or methyl alcohol.

(c) A non-labeled subject

The same things as labeled substances are prepared at 100 to 1000 times higher concentration.

(ii) Assay (a) COS-7 cells expressing polypeptides of the present invention cultured on a 12-well plate for tissue culture are washed twice with assay buffer (1 ml) and then assay buffer is added (490 µl per well).

(b) Labeled subjects (5 µl) are added and the solution is reacted at a room temperature for 1 hour. Non-labeled subjects (5 µl) are added to measure the quantity of unspecific binding.

(c) The reaction solution is removed and the remaining cells are washed with a washing solution (1 ml) 3 times. Labeled subjects bound to cells are dissolved with 0.2M NaOH (included 1% SDS) and the solution is mixed with liquid scintillator A (4 ml) (Wako Pure Chemical Industries, Ltd.).

(d) The radioactivity is measured by liquid scintillation counter (Beckman Coulter).

(13) A Screening Method of Binding Activity Regulatory Substances

A marker of the present invention is useful as a reagent to search or screen binding activity regulatory substances to the markers. As a screening method of binding activity regulatory substances of the markers and binding substances, namely, substances changing the binding activity, a recombinant expression system expressing markers of the present invention is constructed and bioassay system or binding assay system is used. Then substances changing the binding activity between binding substances and markers of the present invention, for example, peptides, proteins, nonpeptide substances, synthetic substances or ferment products can be efficiently screened. The substances comprise a substance which can enhance or reduce (a) cell stimulatory activity between binding substances and a marker of the present invention, for example, an activity to promote or inhibit DNA synthesis monitored by BrdU (bromodeoxyuridine) incorporation or an activity to promote or inhibit of cell migrating activity, or (b) the binding activity between a binding substance and a marker of the present invention.

Namely, the present invention provides with a screening method of binding activity regulatory substances between binding substances and markers of the present invention characterized by comparing the quantity of binding of binding substances when (i) markers of the present invention and binding substances are contacted and (ii) markers of the present invention, binding substances and subjects are contacted.

A screening method of binding activity regulatory substances of the present invention is characteristic of comparing the quantity of binding between the markers and binding substances by measuring, for example, cell stimulatory activity in the case of (i) and (ii).

A screening method of binding activity regulatory substances of the present invention is, for example, (a) a method to screen binding activity regulatory substances which can change the binding activity between binding substances and KIAA1036 polypeptides, comprising measuring and comparing the quantity of binding of labeled substances to the polypeptides when labeled binding substances are contacted to KIAA1036 polypeptides and when labeled binding substances and subjects are contacted, (b) a method to screen binding activity regulatory substances which can change the binding activity between binding substances and polypeptides of the present invention comprising measuring and comparing the quantity of binding of label binding substances to the polypeptides in the cells or cell culture when cells expressing KIAA1036 polypeptides or the cell culture solution and labeled binding substances are contacted and when labeled binding substances and subjects are contacted or (c) a method to screen binding activity regulatory substances which can change the binding activity between binding substances and KIAA1036 polypeptides comprising measuring and comparing the quantity of binding of label binding substances to the polypeptides when polypeptides secreted in cell culture solutions by culturing transformants having KIAA1036 polynucleotides and label binding substances are contacted and when label binding substances and subjects are contacted.

(14) A Kit for Screening of Binding Activity Regulatory Substances

A kit for screening of binding activity regulatory substances changing the binding activity between KIAA1036 polypeptides and binding substances is a kit comprising cells including the polypeptides or a cell culture solution. The examples of a kit for screening of the present invention are the followings.

(i) A Reagent for Screening of Binding Activity Regulatory Substances

As a screening solution and washing solution, a solution that Hank's Balanced Salt Solution (Invitrogen) added 0.05% cattle serum albumin (SIGMA-Aldrich) is sterilized by filtration with 45 □m filter, and it is kept at 4° C. or prepared just before use.

(a) KIAA1036 Polypeptide

COS-7 cells expressing KIAA1036 polypeptides are cultured on a 12 well plate with $5 \times 10^5$ cells/well and cultured at 37° C. for 2 days.

(b) A Labeled Subject

A solution containing commercially available subjects labeled with $^3H$, $^{125}I$, $^{14}C$ or $^{35}S$ is kept at 4° C. or 20° C., and diluted to 1 □ M with assay buffer and prepared just before use. Subjects with the low solubility to water are dissolved in dimethyl formamide, DMSO or methyl alcohol.

(c) A Non-Labeled Subject

The same things with labeled substances are prepared at 100 to 1000 times higher concentration.

(ii) An Assay (a) COS-7 cells expressing polypeptides of the present invention cultured on a 12-well plate for tissue culture are washed twice with assay buffer (1 ml) and then assay buffer is added (490 µl per well).

(b) Labeled subjects (5 □l) are added and the solution is reacted at room temperature for 1 hour. Non-labeled subjects (5 □l) are added to measure the quantity of non-specific binding.

(c) The reaction solution is removed and the remaining cells are washed with a washing solution (1 ml) 3 times. Labeled subjects binding to cells are dissolved with 0.2M NaOH (included 1% SDS) and the solution is mixed with liquid scintillator A (4 ml) (Wako Pure Chemical Industries, Ltd.).

(d) The radioactivity is measured by liquid scintillation counter (Beckman Coulter).

(15) A Screening Method of Expression Regulatory Substances

Polynucleotide A, polypeptide B or antibodies against the polypeptides are useful as a reagent to search or screen expression regulatory substances to markers of the present invention.

Namely, a screening method of expression regulatory substances of the present invention is, for example, a screening method of expression regulatory substances of markers of the present invention by measuring quantity of mRNAs or proteins of KIAA1036 polypeptides or the partial peptides included in (i) blood of a non-human mammal, a specific organ, a tissue or cells isolated from the organ or (ii) transformants and so on.

(16) A Kit for Screening of Expression Regulatory Substances

A kit for screening of expression regulatory substances of KIAA1036 polypeptides or its salt is a kit comprising cells expressing polypeptide A or polypeptide B or cell culture solutions including the polypeptides. The Example of a kit for screening of the present invention is the following.

(17) A Kit for Screening on the Basis of the Immunologic Assay

An assay of KIAA1036 polypeptides is, for example, sandwich ELISA using two kinds of monoclonal antibodies that their epitopes are different in antibodies reacting with the polypeptide in the liquid phase, or a radioimmunoassay using KIAA1036 polypeptides labeled with a radioisotope such as $^{126}I$ and antibodies specifically recognizing it. Therefore, in a case of diagnosis with antibodies, KIAA1036 polypeptide is included as standard antigens in addition to antibodies of the present invention. Furthermore, standard curve can be included in a kit.

(18) A Kit for Screening on the Basis of a Molecular-Biological Assay

The expression level of DNA encoding KIAA1036 polypeptide can be quantitated in mRNA level by Northern hybridization or PCR using oligonucleotides prepared from KIAA1036 polynucleotides.

For example, (i) an agent, for example, an anticancer agent is given into a normal or a disease model non-human mammal (e.g., mouse, rat, rabbit, sheep, pig, cattle, cat, dog or monkey) and after a fixed time, blood, a specific organ, for example, brain, kidney, colon, ovary, tissues or cells isolated from an organ are obtained. mRNAs of a polypeptide of the present invention or the partial peptide included in the obtained cells can be for example, extracted by the extraction method widely known in this field, quantitated by the method such as TaqManPCR or analyzed by Northern blot widely known, or (ii) transformants expressing KIAA1036 polypeptides or the partial peptides are produced by the above mentioned method and mRNAs of KIAA1036 polypeptides or the partial peptides included in the transformant can be quantitated/analyzed.

And in a case of diagnosis with polynucleotides, labeled KIAA1036 polynucleotides are included in a kit.

(19) A Pharmaceutical Composition

A pharmaceutical composition comprising at least one selected from substances such as polynucleotide A, a complementary polynucleotide to the polynucleotide, polypeptide B, its antibody or a gene therapeutic vector having polynucleotide A can be given independently as a therapeutic agent. But preferred is usually that a pharmaceutical composition is mixed with one or more pharmaceutically acceptable carrier(s) and provided as a pharmaceutical preparation produced by the any method widely known in the technical field of galenical pharmacy. Because KIAA1036 inhibit DNA synthesis in vascular endothelial cells and cell migrating activity, DNA synthesis inhibitors and cell migrating activity inhibitors are included. And substances obtained by a screening method or a kit for screening of the present invention and their salts are included. The substance is, for example, (a) a substance enhancing or reducing cell stimulation activity through binding between binding substances and KIAA1036 polypeptides, for example, DNA synthesis activity, migrating activity, network formation activity of vascular endothelial cells, (b) a substance enhancing or reducing a binding activity between a binding substance and KIAA1036 polypeptide or (c) a substance enhancing or reducing an expression level of KIAA1036 polypeptide. The substance is, for example, a low-molecular weight compound, a peptide, a protein, a nonpeptide substance, a synthetic substance or a ferment product. These substances can be new or well-known substances and natural or synthetic substances. Because agonists against KIAA1036 polypeptides have the same activity as bioactivation of binding substances against KIAA1036 polypeptides, they are useful as safe and low-toxic drugs for the binding substance activity. Because antagonists against KIAA1036 polypeptides can inhibit bioactivation of binding substances against KIAA1036 polypeptides, they are useful as safe and low-toxic drugs, which inhibit the binding substance activity. Substances enhancing binding activity between binding substances and KIAA1036 polypeptides are useful as safe and low-toxic drugs to enhance bioactivation of binding substances against KIAA1036 polypeptides. Substances reducing binding activity between binding substances and KIAA1036 polypeptides are useful as safe and low-toxic drugs to reduce bioactivation of binding substances against KIAA1036 polypeptides. And gene therapeutic expression vectors expressing KIAA1036 are included. Because KIAA1036 can be a marker for neovascularization, vascular disease, inflammatory disease, entoptic neovascular disease, reproductive system disease, central nervous system disease or cancer, it is suggested that KIAA1036 relates to those diseases and they are useful for gene therapies of these diseases. The gene therapeutic expression vectors are expression vectors having a part or all of a polynucleotide of KIAA1036 and when they are introduced into cells or tissues, they can normalize disorders which cause some natural or acquired disease at a gene level. In other words, the vectors can compensate for cells with normal genes, repair/modify defects of genes and regulate expression of genes.

(20) A Therapeutic Agent

A pharmaceutical composition comprising polypeptide B, an antibody against the polypeptide, polynucleotide A, complementary polynucleotide to the polynucleotide, a binding substance, a bond regulatory substance, an expression regulatory substance, a DNA synthesis inhibitor, a cell migrating activity inhibitor or a gene therapeutic vector can be given independently as a therapeutic agent. But preferred is usually that a pharmaceutical composition is mixed with one or more pharmaceutically acceptable carrier(s) and provided as a pharmaceutical preparation produced by the any method widely known in the technique field of galenical pharmacy.

The most effective route of administration in treats is desirable as a route of administration, for example, an oral administration or a non-oral administration such as intraoral, tracheobronchial, intrarectal, subcutaneous, intramuscular or intravenous. A form of administration is, for example, spray, capsule, tablet, granule, syrup, emulsion, suppository, injection, ointment or tapes.

An appropriate pharmaceutical preparation for an oral administration is, for example, emulsion, syrup, capsule, tablet, powder or granule. For example, a liquid preparation such as emulsion or syrup can be produced by using water, saccharide such as sucrose, sorbitol or fructose, glycol such as polyethylene glycol or propylene glycol, oil such as sesame oil, olive oil or soybean oil, antiseptic such as p-hydroxy ester benzoate or flavor such as strawberry or peppermint as a excipient. Capsule, tablet, powder or granule can be produced by using a vehicle such as lactose, dextrose, sucrose or mannitol, a disintegrating agent such as starch or sodium alginate, a lubricant such as magnesium stearate or talc, a binding agent such as polyvinyl alcohol, hydroxypropylcellulose or gelatin, a surface active agent such as fatty acid ester or a plasticizer such as glycerol as a excipient.

An appropriate pharmaceutical preparation for non-oral administration is, for example, injection, suppository or spray. For example, an injection is prepared by using a carrier comprising salt solution, dextrose solution or their mixture. A suppository is prepared by using a carrier such as cacao butter, fat hydride or carboxylic acid. And a spray is prepared by using the substance or a carrier, which does not stimulate oral cavity and airway mucous membrane of a recipient and spread the substance as microparticles to become easy to absorb. The carrier includes, for example, lactose or glycerol. A pharmaceutical preparation such as aerosol or dry powder is possible if a nature of the substance and that of the used carrier are appropriate for it. And in these non-oral agents, a component used as an excipient in oral agents can be added.

A substance obtained by using a screening method or a kit for screening of the present invention or the salt is a binding substance, a binding activity regulatory substance, an expression regulatory substance, a DNA synthesis inhibitor or a cell migrating activity inhibitor, for example, (a) a substance enhancing or reducing cell stimulation activity through bonds between binding substances and polypeptide B, for example, an activity to promote or inhibit DNA synthesis, which can be monitored by BrdU (bromodeoxyuridine) uptake, or an activity to promote or inhibit of cell migrating activity, (b) a substance enhancing or reducing a binding activity between binding substances and polypeptide B or (c) a substance enhancing or reducing an expression level of a marker of the present invention.

The substance is a low-molecular weight compound, peptide, protein, non-peptide substance, a synthetic substance or a ferment product. These substances can be new or well-known substances and natural or synthetic substances. Because agonists against KIAA1036 polypeptides have the same activity as bioactivation of binding substances against KIAA1036 polypeptides, they are useful as safe and low-toxic drugs for the binding substance activity. Because antagonists against KIAA1036 polypeptides can inhibit bioactivation of binding substances against KIAA1036 polypeptide or something like this, they are useful as safe and low-toxic drugs, which inhibit the binding substance activity. Substances enhancing binding activity between binding substances and KIAA1036 polypeptides are useful as safe and low-toxic drugs to enhance bioactivation of binding substances against KIAA1036 polypeptides. Substances reducing binding activity between binding substances and KIAA1036 polypeptides are useful as safe and low-toxic drugs to reduce bioactivation of binding substances against KIAA1036 polypeptides. And therapeutic agent KIAA1036 polypeptides for any kinds of diseases comprising substances changing the expression level of KIAA1036 polypeptides seem to have any important role, for example, a central nervous system as described above. Therefore an expression regulatory substance changing the expression level of KIAA1036 polypeptides or the partial peptide can be used as a therapeutic agent for a disease related insufficiency of KIAA1036 polypeptides. When the substance is used as a therapeutic agent for a disease relating insufficiency of KIAA1036 polypeptide, it can be turned a pharmaceutical preparation by the stereotyped method. For example, the substance can be used orally as a tablet with sugar-coating, a capsule, an elixir or a microcapsule as occasion demands or parentally as a sterile solution with water or the other pharmaceutically acceptable solution or an injection of suspension. For example, the substances can be produced by mixing as the unitary dose form required to accomplish popularly acceptable pharmaceutical preparation with physiologically acceptable well-known carrier, spice, vehicle, antiseptic, stabilizer or binding agent. The amount of active principle in these pharmaceutical preparations is decided to be able to obtain an appropriate capacity in a directed range.

An excipient, which can mix with tablet or capsule, is, for example, a binding agent such as gelatin, corn starch, tragacanth or Arabian gum, a vehicle such as crystal cellulose, a swelling agent such as corn starch, gelatin or alginic acid, a lubricant agent such as magnesium stearate, a sweetening agent such as sucrose, lactose or saccharin or a spice such as peppermint or cherry. In the case where the dosage form is a capsule, the above type of ingredients and a liquid carrier such as fat and oil can be included. An aseptic composition for the injection can be prescribed by the usual pharmaceutical preparation, for example, by dissolving or suspending an activity substance in vehicle such as water for the injection or natural plant oil such as sesame oil or coconut oil. An aqueous solution for the injection is, for example, an isotonic solution such as D-sorbitol, D-mannitol or sodium chloride including physiological salt solution, dextrose or adjuvant. It can be used with appropriate solubilizing agent, for example, alcohol such as ethanol, propylene glycol or polyethylene glycol, a nonionic surface-active agent such as polysorbate 80 or HCO-50. Oil solution is, for example, sesame oil or soybean oil and it can be used with a solubilizing agent such as benzyl benzoate or benzyl alcohol.

And the above preventive/therapeutic agent can be mixed with, for example, a buffer such as phosphate buffer or sodium acetate buffer, a soothing agent such as benzalkonium chloride or procaine hydrochloride, a stabilizer such as human serum albumin or polyethylene glycol, a preservatives such as benzyl alcohol or phenol or an antioxidant. A prepared injection solution is usually filled up into an appropriate ampoule.

(21) A Method of Treating

Because the above-mentioned pharmaceutical composition can be a therapeutic agent for vascular disease, inflammatory disease, entoptic neovascular disease, reproductive system disease, central nervous system disease or cancer, a method of treating disease such as vascular disease, inflammatory disease, entoptic neovascular disease, reproductive system disease, central nervous system disease or cancer is provided by giving that pharmaceutical composition by an appropriate method. It is desirable that the above-mentioned pharmaceutical composition is used in the most effectively medication method in treats. And the method is, for example, an oral administration or a non-oral administration such as intraoral, tracheobronchial, intrarectal, subcutaneous, intramuscular or intravenous.

A therapeutic agent as described above is safe and low-toxic and can be given to, for example, a mammal such as human, rat, mouse, rabbit, sheep, pig, cattle, cat, dog or monkey. A dosage of a preventive or therapeutic agent per 1 time varies depending on medication subject, an object organ, a condition of a disease or a medication method. But in the case of a oral administration, for example, for a patient with hypertonia whose body weight is 60 kg, usually approximately 0.1 to 100 mg per a day, preferably approximately 1.0 to 50 mg, more preferably approximately 1.0 to 20 mg are given. For example, in the case of an injection of parentally giving, for example, for a patient with hypertonia whose body weight is 60 kg, usually approximately 0.01 to 30 mg per a day, preferably approximately 0.1 to 20 mg, more preferably approximately 0.1 to 10 mg are given by an intravenous injection. In the case of the other animal, the amount converted into the amount per kg of body weight can be given. The dosage or times of a dosage varies depending on treating effect targeted, medication method, treating period, age or body weight, but usually it is 10 μg to 8 mg/kg per a day for an adult.

EXAMPLES

The following examples are provided to exemplify and do not restrict the present invention. As a genetic engineering method, if there is not a special provision, the method described in Molecular Cloning: A Laboratory Manual, 2nd Edition (Cold Spring Harbor Laboratory). is used.

Example 1

An Identification of Gene Whose Expression in Human Umbilical Vein Endothelial Cells (HUVEC) is Enhanced by the Stimulation of Vascular Endothelial Cell Propagation Factors (VEGF)

Three Endocell HUVEC (KURABO) which is a human umbilical vein vascular endothelial cell were thawed and then inoculated on 16 culture plates coating with collagen (IWAKI) poured EBM medium including 10% fetal calf serum (FCS) (Sanko Junyaku). After culturing at 37° C. for 3 days, the medium was changed with the same medium and cultured for 2 days. After the cells reached to confluence, the medium was changed with M199 medium including 1% FCS (Nissui) and cells were cultured for 24 hours. For a culture with VEGF treatment, the medium was changed to M199 medium including 1% FCS and 1 nM human $VEGF_{165}$ (R&D Systems). For a culture without VEGF (a control), medium was changed with the same medium not including human $VEGF_{165}$. Cells were cultured at 37° C. and collected after 0 hour, 0.5 hours, 2 hours, 6 hours, 12 hours and 24 hours. Collected cells were washed with PBS twice and total RNA were prepared by ISOGEN (Nippon Gene) and mRNAs were prepared by oligo dT cellulose column. These mRNAs were analyzed by LifeArrayhumanUniGENE (Incyte Genomics) through Gene Expression Microarray analysis on assignment of Incyte Genomics.

As a result, for 6393 human genes, gene expression level was calculated as a ratio of a expression level in VEGF-treated cells compared to one in untreated cells in each time point. Among these genes, the expression level of a gene GenBank ID: AF055021, whose function was unknown, was increased by treatment with VEGF reaching the expression level of was 3.8 fold after 24 hours. Because a protein translated region was unclear from the information of sequence of AF055021 gene in a database of NCBI (National Center for Biotechnology Information), a base sequence of the same gene was searched with AssEst (maze) database and a consensus sequence of EST cluster was obtained. Based on this consensus sequence, homology search using Blastx database in AssEst revealed that it encoded KIAA1036 polypeptide (SEQ ID NO: 2) whose function was unknown. Additionally, it had 58% homology with a polypeptide of AK022567 whose function was unknown (FIG. 1). KIAA1036 gene and AK022567 gene on NCBI database have open reading frames corresponding to 365 and 290 amino acid residues respectively, which are initiated from translation initiation codons and they are seem to be almost full length cDNA. A polypeptide of AK022567 was already published internationally as a secretory protein (WO99/3881). And KIAA1036 is predicted as a secretory protein because the homology of their amino acid sequences is 58%.

Example 2

Expression of KIAA1036 in Human Normal Tissues

Cloning of KIAA1036 gene from human umbilical vein vascular endothelial cell was tried. Two kinds of oligonucleotides were synthesized as primers for PCR on the basis of a nucleic acid sequence of 3' untranslated region of KIAA1036 gene from NCBI database.

```
Primer1:
5'-GTTCAGGACTGTCTTTCAGC-3'      (SEQ ID NO: 4)

Primer2:
5'-GTCAATACTGATGGACTTGC-3'      (SEQ ID NO: 5)
```

Total RNA was prepared according to an attached manual with RNeasy Midi (QIAGEN) from HUVEC which are human umbilical vein vascular endothelial cells. Single strand cDNA fragments were prepared from the obtained total RNA (10 □g) with SuperscriptII (Invitrogen). The obtained single strand cDNAs were used as templates and gene fragments were amplified with Primer1 (SEQ ID NO: 4) and Primer2 (SEQ ID NO: 5) by PCR.

To one fiftieth of single strand cDNAs, was added TaKaRa Ex Taq (TaKaRa) (1.25 unit), Primer1 and Primer2 (1 □M each), a buffer ($Mg^{2+}$ plus) for PCR reaction attached TaKaRa Ex Taq (5 □l) and dNTP Mixture whose final concentration was 200 □M. Distilled water was added to the mixture to be 50 □l in total. This was how samples for PCR were prepared. PCR reaction was held under the condition that is 94° C. for 3 minutes was once and the cycle (94° C. for 1 minute, 50° C. for 1 minute and 72° C. for 1 minute) was 30 times and then 72° C. for 5 minutes was once. The amplified cDNA fragment by the PCR reaction was separated by an agarose electrophoresis and 750 bp cDNA fragment (SEQ ID NO: 6) was collected. The obtained cDNA fragment was digested with restriction enzymes, ApaI, HincII and PstI and the lengths of cDNA fragments separated by an agarose gel electrophoresis were measured. And the collected cDNA fragment was confirmed as a target. The cDNA fragment (50 ng) amplified with Primer1 and Primer2 was labeled with $^{32}P$ using [□-$^{32}P$] dCTP (3000 Ci/m mol, 10 mCi/ml) (Amersham Pharmacia Bioteque) by an attached manual with Rediprime II DNA Labeling System (Amersham Pharmacia Bioteque). Northern blot was held with these cDNA fragments labeled with $^{32}P$ as a probe.

Nylon membrane of Multiple Tissue Northern (MTN) Blots Human 12-Lane MTN Blot (Clontech) was immersed with GMC buffer (including 0.5M phosphoric acid buffer, pH 7.2, 1% cattle serum albumin, 1 mM EDTA and 7% SDS) and prehybridization was held at 65° C. for 1 hour. After that, the nylon membrane was immersed with GMC buffer containing probes labeled with $^{32}P$ and hybridization was held at 65° C. for 16 hours. After hybridization, the nylon membrane was washed with 2×SSC (1×SSC was 15 mM sodium citrate, 150 mM NaCl, pH7.0) at a room temperature for 5 minutes, 1×SSC (including 0.2% SDS) at 50° C. for 30 minutes and 0.5×SSC (including 0.2% SDS) at 50° C. for 30 minutes one after another and dried with air. Subsequently, this nylon membrane was put on an imaging plate cassette (FUJI FHOTO FILM CO., LTD.) with an imaging plate (FUJI FHOTO FILM CO., LTD.). Image analysis was held with image analyzer FLA3000 (FUJI FHOTO FILM CO., LTD.).

As a result, signals which showed about 6 kb length were detected from brain, heart, skeletal muscle, spleen, kidney, liver, small intestine and placenta and the strong expression was selectively observed in brain and placenta.

Example 3

Expression of KIAA1036 in Human Umbilical Vein Endothelial Cells

As the VEGF-induced expression of KIAA1036 was originally found by Gene Expression Microarray Analysis using DNA chip as described in Example 1, the result was confirmed by Northern blot with KIIA1036 probe and total RNA prepared from VEGF-treated HUVEC. Endocell HUVEC (KURABO) which are human umbilical vein endothelial cells were cultured in M199 medium containing 1 nM human $VEGF_{165}$ (R&D Systems) and 1% FCS as described in Example 1. After 0, 0.5, 1, 2, 6, 12 and 24 hours of culture, total RNA was prepared from these cells according to an attached manual with RNeasy Midi (QIAGEN).

After electrophoresis of each RNA sample (5 □g), the samples were transferred to a nylon membrane, Hybond-XL (Amersham Pharmacia Bioteque). That nylon membrane was immersed with GMC buffer and prehybridization was held at 65° C. for 1 hour. After prehybridization, the nylon membrane was immersed with GMC buffer containing probes labeled with $^{32}P$ as Example 2 and hybridization was held at 65° C. for 16 hours. After hybridization, the nylon membrane was washed with 2×SSC at a room temperature for 5 minutes, 1×SSC (including 0.2% SDS) at 50° C. for 30 minutes and 0.5×SSC (including 0.2% SDS) at 50° C. for 30 minutes one after another and dried with air. Subsequently, this nylon membrane was put on an imaging plate cassette (FUJI FHOTO FILM CO., LTD.) with an imaging plate (FUJI FHOTO FILM CO., LTD.). Image analysis was held with image analyzer FLA3000 (FUJI FHOTO FILM CO., LTD.).

Next, probes were dehybridized by immersing the same nylon membrane in a bath with boiling water and Northern blot was held with human □-actin cDNA fragments labeled with $^{32}P$ as Example 2 as probes. Signal intensities of KIAA1036 gene were normalized with that of □-actin gene at each time point. And then a ratio of the expression level of KIAA1036 in each time point to 0 hour was calculated.

As a result, the expression was inhibited at 0.5 to 2 hours after adding VEGF but a high gene expression, which was 3.2 fold, was induced after 24 hours. This result was same as that obtained by DNA chip (FIG. 2).

Example 4

Expression of KIAA1036 in Human Cancer Tissues

The difference of expression levels of the genes in a normal tissue and a cancer tissue of all kinds of organ from human was analyzed.

Matched Tumor/Normal Expression Array (Clontech), which is a nylon membrane with cDNAs synthesized from a cancer tissue and a normal tissue of chest, uterus, colon, stomach, ovary, lung, kidney, rectum, cervix, small intestine or prostate of the same patient, was immersed with GMC buffer containing probes labeled with $^{32}P$ as Example 2 and hybridization was held at 65° C. for 16 hours. After hybridization, the nylon membrane was washed with 2×SSC at a room temperature for 5 minutes, 1×SSC (including 0.2% SDS) at 50° C. for 30 minutes and 0.5×SSC (including 0.2% SDS) at 50° C. for 30 minutes one after another and dried with air. Subsequently, this nylon membrane was put on an imaging plate cassette (FUJI FHOTO FILM CO., LTD.) with an imaging plate (FUJI FHOTO FILM CO., LTD.). Image analysis was held with image analyzer FLA3000 (FUJI FHOTO FILM CO., LTD.).

After hybridization of the nylon membrane, signal intensities were measured with □-actin genes labeled with $^{32}P$ as probes as described in Example 3. Signal intensities of KIAA1036 was normalize with signal intensities by □-actin probe in each organ, and a ratio of cancer tissues to normal tissues in the same patient was calculated. Then a change of an expression level of the genes in all kinds of cancer tissue was analyzed.

As a result, expression of KIAA1036 genes were increased in cancer tissues of all 4 patients with ovarian cancer and 11 patients with colon cancer patient (FIG. 3).

Example 5

Expression of KIAA1036 in COS Cells cDNA encoding the polypeptide that 3×FLAG sequence was added to a carboxy-terminal of KIAA1036 amino acid sequence as set forth in Met of 1-Val of 365 of SEQ ID NO: 2 was inserted to a expression vector in animal cells and expressed in COS cells.

A base sequence as set forth in A of 386-C of 1480 of SEQ ID NO: 1 encoding KIAA1036 was inserted in the NotI/XbaI sites of an expression vector in animal cells, p3☐ FLAG-CMV-13 and p3☐FLAG-CMV-14(SIGMA-Aldrich) and plasmids, pFLAG13-1036 and pFLAG14-1036 which express polypeptides that 3☐FLAG was added to carboxy- or amino-terminals of KIAA1036, respectively, were constructed.

COS-7 cells (African green monkey kidney cells (SV40-transformed cells)) were used as host of pFLAG13-1036 and pFLAG14-1036 and transformation was operated by an attached manual with FuGENE6 reagent (Roche Diagnostics).

COS-7 cells (5×10$^5$ cell/well in 60 mm dishes) were cultured in D-MEM medium containing 10% FCS at 37° C. for 16 hours. After medium was changed, pFLAG13-1036 (2 ☐g) and FuGENE6 (10 ☐l) were added to the cells and the cells were cultured for 48 hours. pFLAG14-1036 and p3×FLAG-CMV-14 without KIAA1036 cDNA as a control were also used in a same method to make transfectants and the transfectants were cultured.

Expression of KIAA1036 polypeptide fused with FLAG was analyzed by Western blotting, a method of Laemli.

The culture supernatants (10 µl) of all kinds of COS-7 transfectants were subjected to SDS-PAGE and electrically transferred to a nitrocellulose membrane in a nitrocellulose membrane kit (TEFCO). The nitrocellulose membrane was immersed with a blocking reagent (TBS, pH7.6; including 5% (w/v) skim milk) and shook at a room temperature for 1 hour. And the membrane was immersed in TBS reagent (pH7.6; including 5% (w/v) skim milk) containing anti-FLAG M2 antibody labeled with peroxidase (HRP) (SIGMA-Aldrich), put static at a room temperature for 1 hour. Then the nitrocellulose membrane was washed with a washing reagent (TBS, pH7.6; including 0.05% (v/v) TritonX-100) for 10 minutes 3 times. The nitrocellulose membrane and ECL Plus Western Blotting Detection Reagents (Amersham Pharmacia Bioteque) were reacted at a room temperature. The nitrocellulose membrane and X-ray film X-OMAT AR (Kodak) were put on X-OMAT cassette (Kodak) immediately and exposed for a few minutes.

As a result, expected bands, which show about 50 kDa, from the culture supernatant of COS cells transfected with pFLAG13-1036 and pFLAG14-1036 were detected but the band was not detected in a control. Therefore, it was confirmed that KIAA1036 gene encodes a KIAA1036 protein, which is able to express, and that KIAA1036 was a secretory protein in animal cells.

Example 6

Expression of KIAA1036 Protein in a Baculovirus System

Expressions in a baculovirus system were operated with Bac-to-Bac Baculovirus Expression System (Invitrogen) according to an attached manual.

cDNA fragments encoding KIAA1036 with 3×FLAG at the carboxy-terminal described in Example 5 was inserted in NotI/XhoI sites of a plasmid pFastBac1, an expression plasmid for insect cells, to make pFASTBac1036. The recombinant plasmid was introduced in Max Efficiency DH10 Bac Competent Cells and cDNA was transferred into baculovirus genome (bacmid DNA) to give rise to a recombinant bacmid DNA. The recombinant bacmid DNA was introduced in Sf9 (ATCC: CRL-1711, ovary cell) cell with CellFECTIN Reagent (Invitrogen) to obtain a recombinant baculovirus. A culture supernatant (0.5 ml) of Sf9 transfectants was added into a culture medium (50 ml) of Sf9 cells with vascular disease, inflammatory disease, entoptic neovascular disease, reproductive system disease, central nervous system disease or malignant neoplasma (The concentration was 1.5×10$^6$ cells/ml) and cultured at 28° C. for 96 hours. The transformed cells were collected by centrifugation. Expression of the FLAG-tagged KIAA1036 was confirmed by Western blotting as described in Example 5.

The collected transformants were washed once with PBS (5 ml, pH7.4). After washing, the cells were suspended in Lysis reagent (5 ml) (including 50 mM Tris-HCl, pH7.4; 0.15M NaCl, 0.1 mM EDTA/2Na, 0.1 mM EGTA, 1 mM DTT, 0.1 mM Amidinophenyl methansulfonylflouride hydrochloride or 0.1% NP-40), treated with ultrasonic waves on ice for 15 seconds for 4 times by MICROCON (HEART SYSTEMS) and separated by centrifugation at 14,500×g for 20 minutes. The same amount of Lysis reagent was added to the supernatant to make it a crude protein solution.

After a crude protein solution (10 ☐l) was subjected to SDS-PAGE, it was electrically transferred on a nitrocellulose membrane in nitrocellulose membrane kit (TEFCO). The nitrocellulose membrane was immersed in a blocking reagent (TBS, pH7.6; including 5% (w/v) skim milk) and shook at a room temperature for 1 hour. After that, it was immersed in a TBS reagent (pH7.6; including 5% (w/v) skim milk) containing anti-FLAG M2 antibody labeled with peroxidase (HRP) (SIGMA-Aldrich), put static at a room temperature for 1 hour. And then the nitrocellulose membrane was washed with the washing reagent (TBS, pH7.4; including 0.05% (v/v) TritonX-100) for 10 minutes 3 times. The nylon membrane and ECL Plus Western Blotting Detection Reagents (Amersham Pharmacia Bioteque) were reacted at a room temperature. The nitrocellulose membrane and X-ray hyper film ECL (Amersham Pharmacia Bioteque) were put on X-OMAT cassette (Kodak) immediately and exposed for a few minutes.

KIAA1036FLAG proteins were purified by an affinity chromatography with anti-FLAG antibodies.

After an ANTI-FLAG M2-Agarose (SIGMA-Aldrich) affinity column was equilibrated with TBS, pH7.4 (including 0.1% NP-40), a crude protein solution was added and FLAG proteins were separated. The columns were then washed with TBS (pH7.4; including 0.1% NP-40) and the protein was eluted with Gly-HCl (pH3.5; including 0.1% NP-40) to be 1 ml/fraction. Each fraction was neutralized with 1M Tris-HCl (pH8.0; 20 ☐l) to make it an affinity purification fraction.

A crude protein fraction (10 ☐l) and an affinity purified fraction (10 ☐l) were subjected to SDS-PAGE and the gel was stained by Bio-Safe Coomassie (BIO-RAD).

As a result, an expected band with about 50 kDa was detected.

Furthermore, after SDS-PAGE, the purified fraction was electrically transferred to PVDF membrane (BIO-RAD) and a band stained with Bio-Safe Coomassie (BIO-RAD) was cut off, and then a sequence of an amino terminal was analyzed by an amino acid sequencer, Procise Model 491 (Applied Biosystems).

As a result, an amino acid sequence as set forth in Pro of 2-Gly of 10 of SEQ ID NO: 2 was detected and it was confirmed that the expressed protein was KIAA1036.

Example 7

A Blocking Effect of DNA Synthesis by KIAA1036 in Vascular Endothelial Cells

To examine an effect of KIAA1036 protein to the proliferation of vascular endothelial cells, BrdU (bromodeoxyuridine) incorporation was measured in HUVEC cells treated with VEGF in the presence (a treated group) or the absence (a control group) of KIAA1036. A KIAA1036 protein, which was expressed by a baculovirus expression system in Example 6 and purified by an affinity chromatography, was used. Incorporation of BrdU into cells was measured with cell propagation ELISA and a BrdU chemiluminescence kit according to an attached manual.

Endocell HUVEC (KURABO) which are human vascular endothelial cells (3000 cells/plate) were cultured on collagen-coated plates (IWAKI) with M199 medium (Nissui) containing 5% fetal calf serum (FCS) at 37□ for 24 hours. For the VEGF-treated group, medium was changed to M199 medium including 1% FCS, 1 nM human $VEGF_{165}$ (R&D Systems) and 0, 1, 10 nM KIAA1036 protein. For the VEGF-untreated group (control group) medium was changed to the same mediums without human $VEGF_{165}$ containing 0, 1 or 10 nM KIAA1036 protein. A solution labeled with BrdU (0.02 ml/well) was added and the cells were cultured at 37□ for 12 hours. The cultured cells were put static at a room temperature for 1 hour to immobilize and an anti-BrdU antibody solution labeled with POD (0.1 ml/well) was added and the cells were put static at a room temperature for 1 hour. The cells were washed with a washing buffer for 5 minutes 3 times and a luminecsence substrate (0.1 ml/well) was added. After 3 minutes of shaking, the instantaneous fluorescence for 5 seconds was measured by Luminescencer JNR (ATTO) within 10 minutes.

Figure 4:
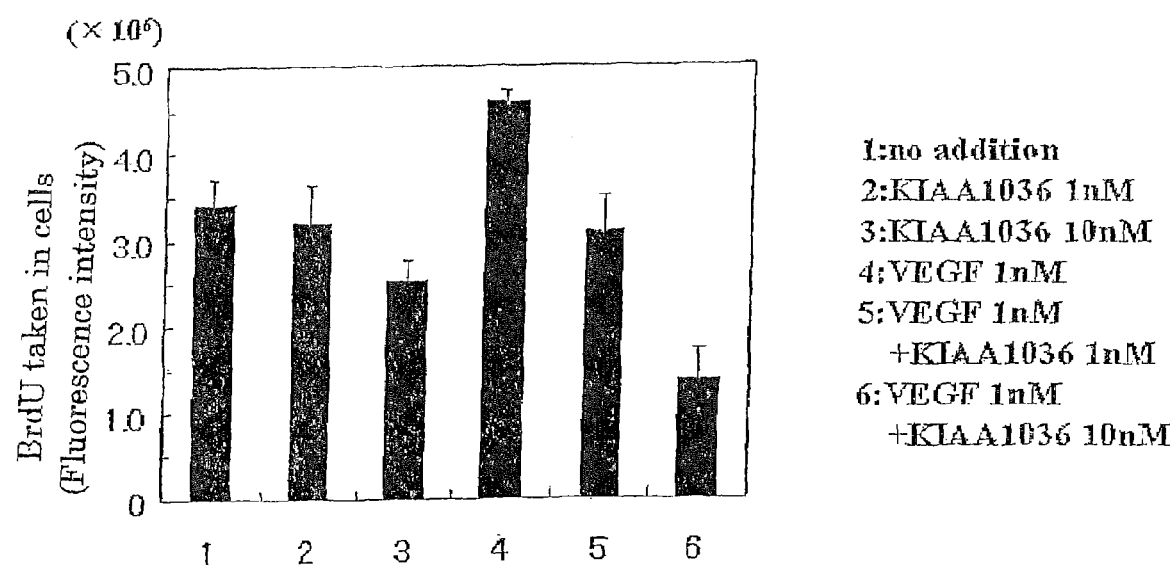
FIG. 4 shows a cytostatic effect of KIAA1036 polypeptide against a vascular endothelial cell.
Cell propagation in human vascular endothelial cells was calculated by measuring an uptake of bromodeoxyuridine (BrdU) in DNA synthesis. Human vascular endothelial cells were divided in M199 medium in which a concentration of KIAA1036 polypeptide was 0, 1 or 10 nM. BrdU reagent was added thereto and the cells were cultured for 12 hours. And then the quantity of BrdU taken in cells was measured (lane 1 to 3). The same operation was carried out with M199 medium to which 1 nM VEGF was added and the quantity of BrdU taken in cells was measured (lane 4 to 6).
As a result, regardless of the addition of VEGF, DNA synthesis in cells was decreased, depending on the concentration of added KIAA1036 polypeptide.

As a result, VEGF promoted DNA synthesis of HUVEC, but KIAA1036 protein doses-dependently inhibited it (FIG. 4).

Example 8

A Blocking Effect to the Migration of Vascular Endothelial Cells by KIAA1036 Protein An effect to the migration of vascular endothelial cells of KIAA1036 protein was examined by a modified Boyden chamber method.

To the lower chambers of Transwell (Corning coaster), M199 medium (600 □l/well) containing 0.25 nM human $VEGF_{165}$ (R&D Systems) and 1 or 10 nM KIAA1036 protein was added for samples treated with VEGF (test group), and M199 medium (600 □l/well) containing 1 or 10 nM KIAA1036 protein without VEGF was added for a control group. Endocell HUVEC (KURABO) ($4 \times 10^4$ cells/well) were cultured in M199 medium containing 5% FCS for 16 hours and then seeded in the upper chambers and cultured at 37□ for 4 hours. Filters of Transwell were immobilized with Diffquick fix reagent (Sysmex) and then stained with Diffquick stain (Sysmex). After wiping the side of the upper chamber of filter, the cell migration ability toward VEGF was measured by counting the number of the cells migrating to the lower part.

Figure 5:
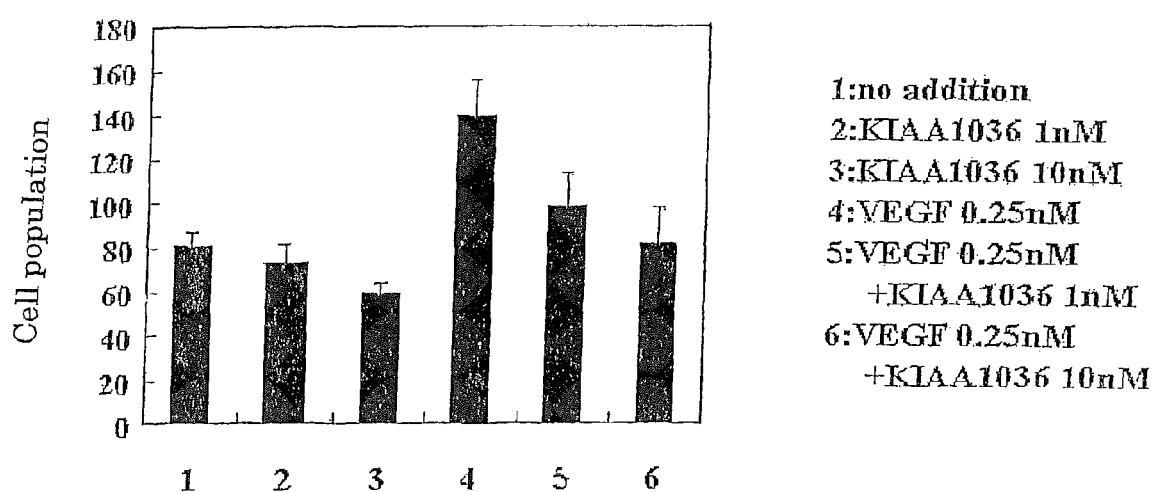
FIG. 5 shows a depression effect of KIAA1036 against migrating activity of a vascular endothelial cell.
M199 medium, in which a concentration of KIAA1036 polypeptide was 0, 1 or 10 nM, was added in the lower layer of a culture apparatus divided with a filter and vascular endothelial cells were added in the upper layer of it. The cells were cultured for 4 hours. Then cell population attached to the filter was measured (lane 1 to 3). The same operation was carried out with M199 medium to which 0.25 nM VEGF was added and cell population attached to the filter was measured (lane 4 to 6).

As a result, VEGF promoted migration of HUVEC, but KIAA1036 protein significantly inhibited it (FIG. 5).

Example 9

A Blocking Effect to Network Formation of Vascular Endothelial Cells by KIAA1036 Protein To examine an effect to network formation of vascular endothelial cells by KIAA1036 protein, network formation of HUVEC in the presence (treated group) or the absence (control group) of KIAA1036 protein was observed.

Matrigel (Becton Dickinson Biosciences) (1 ml/well) was divided in 6-well tissue culture plates chilled on ice and put static at 37□ for 1 hour to be gelatinized. Endocell HUVEC (KURABO) were suspended in EBM medium containing 10% FCS and poured onto the matrigel at $5 \times 10^4$ cells/well with a final concentration of KIAA1036 protein at 1 or 10 nM (test group) or without KIAA1036 protein. After 9 hours of incubation at 37□, the network formations of HUVEC in test divisions and control divisions were observed with an inverted microscope.

As a result, it was confirmed that KIAA1036 protein obviously inhibits the network formation.

INDUSTRIAL APPLICABILITY

The present invention provides with a detection method of mRNA of KIAA1036, a detection method of a polypeptide of KIAA1036, a marker for neovascularization, vascular disease, inflammatory disease, entoptic neovascular disease, reproductive system disease, central nervous system disease or malignant neoplasm, a diagnostic kit and a therapeutic agent.

The invention claimed is:

1. A method for inhibiting proliferation of vascular endothelial cells comprising administering to said vascular endothelial cells: (a) a composition comprising the polypeptide KIAA 1036 having the amino acid sequence of SEQ ID NO:2 or (b) a composition comprising a polynucleotide that encodes and expresses the polypeptide KIAA 1036 having the amino acid sequence of SEQ ID NO: 2 in said vascular endothelial cells.

2. The method of claim 1, in which the composition is administered to a subject or said polynucleotide is expressed in a subject.

3. The method of claim 1, in which the composition is administered to cells in culture or said polynucleotide is expressed in cells in culture.

4. The method of claim 2, in which the subject presents with entoptic neovascularization, colon cancer or ovarian cancer.

5. A method for preventing angiogenesis comprising administering to said vascular endothelial cells: (a) a composition comprising the polypeptide KIAA 1036 having the amino acid sequence of SEQ ID NO: 2 or (b) a composition comprising a polynucleotide that encodes and expresses the polypeptide KIAA 1036 having the amino acid sequence of SEQ ID NO: 2 in said vascular endothelial cells.

6. The method of claim 5, in which the composition is administered to a subject or said polynucleotide is expressed in a subject.

7. The method of claim 5, in which the composition is administered to vascular endothelial cells in culture or said polynucleotide is expressed in cells in culture.

8. The method of claim 6, in which the subject presents with entoptic neovascularization, colon cancer or ovarian cancer.

* * * * *